(12) United States Patent
Smolke et al.

(10) Patent No.: US 10,053,697 B1
(45) Date of Patent: Aug. 21, 2018

(54) PROGRAMMABLE ALTERNATIVE SPLICING DEVICES AND USES THEREOF

(71) Applicant: The Board of Trustees of the Leland Stanford Junior University, Stanford, CA (US)

(72) Inventors: Christina D. Smolke, Menlo Park, CA (US); Melina Mathur, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 154 days.

(21) Appl. No.: 14/991,837

(22) Filed: Jan. 8, 2016

Related U.S. Application Data

(60) Provisional application No. 62/101,921, filed on Jan. 9, 2015.

(51) Int. Cl.
| | | |
|---|---|---|
| *C12P 19/34* | (2006.01) |
| *C12N 15/115* | (2010.01) |
| *C12N 15/85* | (2006.01) |
| *C12Q 1/6897* | (2018.01) |
| *C12N 15/67* | (2006.01) |
| *G01N 33/53* | (2006.01) |

(52) U.S. Cl.
CPC ........... *C12N 15/115* (2013.01); *C12N 15/67* (2013.01); *C12N 15/85* (2013.01); *C12Q 1/6897* (2013.01); *G01N 33/5308* (2013.01); *C12N 2310/12* (2013.01); *C12N 2310/16* (2013.01); *C12N 2310/531* (2013.01); *C12N 2830/42* (2013.01); *C12N 2830/52* (2013.01)

(58) Field of Classification Search
CPC .............. C12N 15/115; C12N 2310/16; C12N 2320/33
USPC ........... 436/6.1, 6.11, 91.1, 91.31, 455, 501; 514/1, 2, 44; 536/23.1, 24.5, 24.1, 25.4; 435/6.1, 6.13, 91.1, 91.31, 320.1, 325, 435/455
See application file for complete search history.

(56) References Cited

U.S. PATENT DOCUMENTS

2009/0170793 A1* 7/2009 Gaur .................... C12N 15/115
514/44 R

OTHER PUBLICATIONS

Culler et al, Science, vol. 330, pp. 1251-1255 (2010).*
Kim et al, BMC Molecular Biol., vol. 9, p. 23 (15 pages) (2008).*
Newman et al, RNA, vol. 12, pp. 1129-1141 (2006).*
Culler, et al, "Functional selection and systematic analysis of intronic splicing elements identify active sequence motifs and associated splicing factors", Nucleic Acids Research, 2010, vol. 38, No. 15, pp. 5152-5165.
Culler, et al, "Reprogramming Cellular Behavior with RNA Controllers Responsive to Endogenous Proteins", Science, vol. 330, 2010, pp. 1251-1255.
Kim, et al. "Ligand-induced sequestering of branchpoint sequence allows conditional control of splicing", BMC Molecular Biology, 2008, 9:23, pp. 1-15.
Liang, et al. "Engineering Biological Systems with Synthetic RNA Molecules", Molecular Cell 43, 2011, pp. 915-926.
Newman, et al. "Identification of RNA-binding proteins that regulate FGFR2 splicing through the use of sensitive and specific dual color fluorescence minigene assays", RNA (2006), 12:1129-1141.
Clancy, "RNA Splicing: Introns, Exons and Spliceosome", Nature Education, 2008, 1(1):31.
Hossain et al., "Using Yeast Genetics to Study Splicing Mechanisms", Methods Mol Biol., 2014, 1126: 285-198.
Kaufer et al., "Survey and Summary—Analysis of the splicing machinery in fission yeast: a comparison with budding yeast and mammals", Nucleic Acids Research, 2000, 28(16): 3003-3010.
Shang et al., "Alternative Splicing in Plant Genes: A Means of Regulating the Environmental Fitness of Plants", International Journal of Molecular Sciences, 2017, 18, 432; doi:10.3390/ijms18020432.

* cited by examiner

*Primary Examiner* — Jane J Zara
(74) *Attorney, Agent, or Firm* — James S. Keddie; Bozicevic, Field & Francis LLP

(57) ABSTRACT

Provided herein, among other things, is an RNA that comprises a first exon, a second exon, a third exon and a fourth exon, wherein the RNA is capable of being spliced into; i. a first splicing product comprising the second exon or ii. a splicing second product comprising the third exon, wherein: i. an intron of the RNA, e.g., the intron between the first and second exons of the RNA, comprises an aptamer and ii. binding of a ligand to the aptamer determines whether the RNA is spliced into the first splicing product or the second splicing product. Methods and cells containing the RNA are also described.

17 Claims, 25 Drawing Sheets

| # | Construct | Splicing outcome | % Range |
|---|---|---|---|
| 1 |  | 1-3-4 | 1-3-4 – 90-100% |
| 2 |  | 1-2-4<br>1-3-4 | 1-2-4 – 0-100%<br>1-3-4 – 0-100% |
| 3 |  | 1-2-4<br>1-3-4 | 1-2-4 – 0-100%<br>1-3-4 – 0-100% |
| 4 |  | 1-2-4<br>1-3-4 | 1-2-4 – 0-100%<br>1-3-4 – 0-100% |
| 5 |  | 1-2-4<br>1-3-4 | 1-2-4 – 0-100%<br>1-3-4 – 0-100% |
| 6 |  | 1-2-4<br>1-3-4 | 1-2-4 – 0-100%<br>1-3-4 – 0-100% |
| 7 |  | 1-2-4<br>1-3-4 | 1-2-4 – 0-100%<br>1-3-4 – 0-100% |
| 8 |  | 1-2-4<br>1-3-4 | 1-2-4 – 0-100%<br>1-3-4 – 0-100% |
| 9 |  | 1-2-4<br>1-3-4 | 1-2-4 – 0-100%<br>1-3-4 – 0-100% |
| 10 |  | 1-2-4<br>1-3-4 | 1-2-4 – 0-100%<br>1-3-4 – 0-100% |
| 11 |  | 1-2-4<br>1-3-4 | 1-2-4 – 0-100%<br>1-3-4 – 0-100% |
| 12 |  | 1-2-4<br>1-3-4 | 1-2-4 – 0-100%<br>1-3-4 – 0-100% |

| 13 |  | 1-2-4<br>1-3-4 | 1-2-4 – 0-100%<br>1-3-4 – 0-100% |
|---|---|---|---|
| 14 |  | 1-2-4<br>1-3-4 | 1-2-4 – 0-100%<br>1-3-4 – 0-100% |
| 15 |  | 1-2-4<br>1-3-4 | 1-2-4 – 0-100%<br>1-3-4 – 0-100% |
| 16 |  | 1-2-4<br>1-3-4 | 1-2-4 – 0-100%<br>1-3-4 – 0-100% |
| 17 |  | 1-2-4<br>1-3-4 | 1-2-4 – 0-100%<br>1-3-4 – 0-100% |
| 18 |  | 1-2-4<br>1-3-4 | 1-2-4 – 0-100%<br>1-3-4 – 0-100% |
| 19 |  | 1-2-4<br>1-3-4 | 1-2-4 – 0-100%<br>1-3-4 – 0-100% |
| 20 |  | 1-2-4<br>1-3-4 | 1-2-4 – 0-100%<br>1-3-4 – 0-100% |
| 21 |  | 1-2-4<br>1-3-4 | 1-2-4 – 0-100%<br>1-3-4 – 0-100% |
| 22 |  | 1-2-4<br>1-3-4 | 1-2-4 – 0-100%<br>1-3-4 – 0-100% |
| 23 |  | 1-2-4<br>1-3-4 | 1-2-4 – 0-100%<br>1-3-4 – 0-100% |
| 24 |  | 1-2-4<br>1-3-4 | 1-2-4 – 0-100%<br>1-3-4 – 0-100% |
| 25 |  | 1-2-4<br>1-3-4 | 1-2-4 – 0-100%<br>1-3-4 – 0-100% |

| 26 |  | 1-2-4 | 1-2-4 – 0-100% |
| | | 1-3-4 | 1-3-4 – 0-100% |
| 27 |  | 1-2-4 | 1-2-4 – 0-100% |
| | | 1-3-4 | 1-3-4 – 0-100% |
| 28 |  | 1-2-4 | 1-2-4 – 0-100% |
| | | 1-3-4 | 1-3-4 – 0-100% |
| 29 |  | 1-2-4 | 1-2-4 – 0-100% |
| 30 |  | 1-3-4 | 1-3-4 – 0-100% |

12G

12H

SEQUENCE LISTING

<160> NUMBER OF SEQ ID NOS: 49

<210> SEQ ID NO 1
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 1
tacgactcac tata                                                      14

<210> SEQ ID NO 2
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 2
tactactcac tata                                                      14

<210> SEQ ID NO 3
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 3
ttttgttttc ttta                                                      14

<210> SEQ ID NO 4
<211> LENGTH: 14
<212> TYPE: DNA
<213> ORGANISM: Artificial sequence
<220> FEATURE:
<223> OTHER INFORMATION: Synthetic nucleotide sequence

<400> SEQUENCE: 4
ttttgtcctc ttta                                                      14

<210> SEQ ID NO 5
<211> LENGTH: 38
<212> TYPE: DNA
<213> ORGANISM: Artificial sequence
<220> FEATURE:
<223> OTHER INFORMATION: Synthetic nucleotide sequence

<400> SEQUENCE: 5
ggcgatacca cgggaaaccg ccttggctgc gccagaga                              38

<210> SEQ ID NO 6
<211> LENGTH: 10
<212> TYPE: DNA
<213> ORGANISM: Artificial sequence
<220> FEATURE:
<223> OTHER INFORMATION: Synthetic nucleotide sequence

<400> SEQUENCE: 6
tctcatttgc                                                             10

<210> SEQ ID NO 7
<211> LENGTH: 70
<212> TYPE: RNA
<213> ORGANISM: Artificial sequence
<220> FEATURE:
<223> OTHER INFORMATION: Synthetic nucleotide sequence

<400> SEQUENCE: 7
cuggcacccg uuuguugugu gucucacacc cgguccaugc cggccgcccg cgcccgcucu       60
ccgcuguccc                                                             70

<210> SEQ ID NO 8
<211> LENGTH: 48
<212> TYPE: RNA
<213> ORGANISM: Artificial sequence
<220> FEATURE:
<223> OTHER INFORMATION: Synthetic nucleotide sequence

<400> SEQUENCE: 8
uuucucuuuc ucucucccuc ccugucuuuc ccucucucuc ucuuuccc                   48

<210> SEQ ID NO 9
<211> LENGTH: 38
<212> TYPE: RNA
<213> ORGANISM: Artificial sequence
<220> FEATURE:
<223> OTHER INFORMATION: Synthetic nucleotide sequence

<400> SEQUENCE: 9
uuucucuuuc ucucucccuc ccugucuuuc ccucucuc                              38

<210> SEQ ID NO 10
<211> LENGTH: 33
<212> TYPE: RNA
<213> ORGANISM: Artificial sequence
<220> FEATURE:
<223> OTHER INFORMATION: Synthetic nucleotide sequence

<400> SEQUENCE: 10
uuucucuuuc ucucucccuc ccugucuuuc ccu                                   33

<210> SEQ ID NO 11
<211> LENGTH: 28
<212> TYPE: RNA
<213> ORGANISM: Artificial sequence
<220> FEATURE:
<223> OTHER INFORMATION: Synthetic nucleotide sequence

<400> SEQUENCE: 11
uuucucuuuc ucucucccuc ccugucuu                                         28

<210> SEQ ID NO 12
<211> LENGTH: 23
<212> TYPE: RNA
<213> ORGANISM: Artificial sequence
<220> FEATURE:
<223> OTHER INFORMATION: Synthetic nucleotide sequence

<400> SEQUENCE: 12
uuucucuuuc ucucucccuc ccu                                              23

<210> SEQ ID NO 13
<211> LENGTH: 18
<212> TYPE: RNA
<213> ORGANISM: Artificial sequence
<220> FEATURE:
<223> OTHER INFORMATION: Synthetic nucleotide sequence

<400> SEQUENCE: 13
uuucucuuuc ucucuccc                                                    18

<210> SEQ ID NO 14
<211> LENGTH: 13
<212> TYPE: RNA
<213> ORGANISM: Artificial sequence
<220> FEATURE:
<223> OTHER INFORMATION: Synthetic nucleotide sequence

<400> SEQUENCE: 14
uuucucuuuc ucu                                                         13

<210> SEQ ID NO 15
<211> LENGTH: 21
<212> TYPE: RNA
<213> ORGANISM: Artificial sequence
<220> FEATURE:
<223> OTHER INFORMATION: Synthetic nucleotide sequence

<400> SEQUENCE: 15
cucggcuccu ccggcuccuc c                                                21

<210> SEQ ID NO 16
<211> LENGTH: 21
<212> TYPE: RNA
<213> ORGANISM: Artificial sequence
<220> FEATURE:
<223> OTHER INFORMATION: Synthetic nucleotide sequence

<400> SEQUENCE: 16
ggcuccuccg gcuccuccga u                                                21

<210> SEQ ID NO 17
<211> LENGTH: 39
<212> TYPE: RNA
<213> ORGANISM: Artificial sequence
<220> FEATURE:
<223> OTHER INFORMATION: Synthetic nucleotide sequence

<400> SEQUENCE: 17
cucggcuccu ccggcuccuc cggcuccucc ggcuccucc                             39

<210> SEQ ID NO 18
<211> LENGTH: 39
<212> TYPE: RNA
<213> ORGANISM: Artificial sequence
<220> FEATURE:
<223> OTHER INFORMATION: Synthetic nucleotide sequence

<400> SEQUENCE: 18
ggcuccuccg gcuccuccgg cuccuccggc uccuccgau         39

<210> SEQ ID NO 19
<211> LENGTH: 603
<212> TYPE: DNA
<213> ORGANISM: Artificial sequence
<220> FEATURE:
<223> OTHER INFORMATION: Synthetic nucleotide sequence

<400> SEQUENCE: 19
atggtgagca agggcgagga gctgttcacc ggggtggtgc ccatcctggt cgagctggac     60
ggcgacgtaa acggccacaa gttcagcgtc cgcggcgagg gcgagggcga tgccaccaac    120
ggcaagctga ccctgaagtt catctgcacc accggcaagc tgcccgtgcc ctggcccacc    180
ctcgtgacca ccttcggcta cggcgtggcc tgcttcagcc gctaccccga ccacatgaag    240
cagcacgact tcttcaagtc cgccatgccc gaaggctacg tccaggagcg caccatctct    300
ttcaaggacg acggtaccta caagacccgc gccgaggtga agttcgaggg cgacaccctg    360
gtgaaccgca tcgagctgaa gggcatcgac ttcaaggagg acggcaacat cctggggcac    420
aagctggagt acaacttcaa cagccacaac gtctatatca cggccgacaa gcagaagaac    480
ggcatcaagg ctaacttcaa gatccgccac aacgttgagg acggcagcgt gcagctcgcc    540
gaccactacc agcagaacac ccccatcggc gacggccccg tgctgctgcc cgacaaccac    600
cag                                                                  603

<210> SEQ ID NO 20
<211> LENGTH: 111
<212> TYPE: DNA
<213> ORGANISM: Artificial sequence
<220> FEATURE:
<223> OTHER INFORMATION: Synthetic nucleotide sequence

<400> SEQUENCE: 20
ctcgtgagca agggcgagga ggataacatg gccatcatca aggagttcat gcgcttcaaa     60
gtgcacatgg agggctccgt gaacggccac gagttcgaga tcgagggcaa g             111

<210> SEQ ID NO 21
<211> LENGTH: 117
<212> TYPE: DNA
<213> ORGANISM: Artificial sequence
<220> FEATURE:
<223> OTHER INFORMATION: Synthetic nucleotide sequence

<400> SEQUENCE: 21
ctgagccatc agtccgcccct gagcaaagac cccaacgaga gcgcgatca catggtcctg     60
ctggagttcg tgaccgccgc cgggattaca catggcatgg acgagctgta caaggat       117

<210> SEQ ID NO 22
<211> LENGTH: 600
<212> TYPE: DNA
<213> ORGANISM: Artificial sequence
<220> FEATURE:
<223> OTHER INFORMATION: Synthetic nucleotide sequence

<400> SEQUENCE: 22
ggcgagggcc gcccctacga gggcacccag accgccaagc tgaaagtgac caagggtggc     60
cccctgccct tcgcctggga catcctgtcc cctcagttca tgtacggctc caaggcctac    120

```
gtgaagcacc cgccgacat ccccgactac ttgaagctgt ccttccccga gggcttcaag    180
tgggagcgcg tgatgaactt cgaggacggc ggcgtggtga ccgtgaccca ggactcctcc    240
ctgcaagacg gcgagttcat ctacaaagtg aagctgcgcg gcaccaactt ccctccgac    300 ggccccgtaa tgcagaagaa gaccatgggc tgggaggcct cctccgagcg gatgtacccc    360
gaggacggcg ccctgaaggg cgagatcaag cagaggctga agctgaagga cggcggccac    420
tacgacgctg aagtcaagac cacctacaag gccaagaagc ccgtgcagct gcccggagcc    480
tacaacgtca acatcaagtt ggacatcacc tcccacaacg aggactacac catcgtggaa    540
cagtacgaac gcgccgaggg ccgccactcc accggcggca tggacgagct gtacaagtaa    600

<210> SEQ ID NO 23
<211> LENGTH: 579
<212> TYPE: DNA
<213> ORGANISM: Artificial sequence
<220> FEATURE:
<223> OTHER INFORMATION: Synthetic nucleotide sequence

<400> SEQUENCE: 23
atggtgagca agggcgagga ggataacatg gccatcatca aggagttcat gcgcttcaaa    60
gtgcacatgg agggctccgt gaacggccac gagttcgaga tcgagggcga gggcgagggc    120 cgccccctacg agggcaccca gaccgccaag ctgaaagtga ccaagggtgg ccccctgccc    180
ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
ggcgagttca tctacaaagt gaagctgcgc ggcaccaact tcccctccga cggccccgta    420
atgcagaaga agaccatggg ctgggaggcc tcctccgagc ggatgtaccc cgaggacggc    480
gccctgaagg gcgagatcaa gcagaggctg aagctgaagg acggcggcca ctacgacgct    540
gaagtcaaga ccacctacaa ggccaagaag cccgtgcag                          579

<210> SEQ ID NO 24
<211> LENGTH: 126
<212> TYPE: DNA
<213> ORGANISM: Artificial sequence
<220> FEATURE:
<223> OTHER INFORMATION: Synthetic nucleotide sequence

<400> SEQUENCE: 24
ctcgtgagca agggcgagga gctgttcacc ggggtggtgc ccatcctggt cgagctggac    60
ggcgacgtaa acggccacaa gttcagcgtc cgcggcgagg gcgagggcga tgccaccaac    120
ggcaag                                                              126

<210> SEQ ID NO 25
<211> LENGTH: 132
<212> TYPE: DNA
<213> ORGANISM: Artificial sequence
<220> FEATURE:
<223> OTHER INFORMATION: Synthetic nucleotide sequence

<400> SEQUENCE: 25
ctgcccggag cctacaacgt caacatcaag ttggacatca cctcccacaa cgaggactac    60
accatcgtgg aacagtacga acgcgccgag ggccgccact ccaccggcgg catggacgag    120
ctgtacaagg at                                                       132
```

<210> SEQ ID NO 26
<211> LENGTH: 594
<212> TYPE: DNA
<213> ORGANISM: Artificial sequence
<220> FEATURE:
<223> OTHER INFORMATION: Synthetic nucleotide sequence

<400> SEQUENCE: 26

```
gctaccctga agttcatctg caccaccggc aagctgcccg tgccctggcc caccctcgtg      60
accaccttcg gctacggcgt ggcctgcttc agccgctacc ccgaccacat gaagcagcac     120
gacttcttca gtccgccat gcccgaaggc tacgtccagg agcgcaccat ctctttcaag      180
gacgacggta cctacaagac ccgcgccgag gtgaagttcg agggcgacac cctggtgaac     240
cgcatcgagc tgaagggcat cgacttcaag gaggacggca acatcctggg gcacaagctg     300
gagtacaact tcaacagcca caacgtctat atcacggccg acaagcagaa gaacggcatc     360
aaggctaact tcaagatccg ccacaacgtt gaggacggca gcgtgcagct cgccgaccac     420
taccagcaga cacccccat cggcgacggc cccgtgctgc tgcccgacaa ccactacctg      480
agccatcagt ccgccctgag caaagacccc aacgagaagc gcgatcacat ggtcctgctg     540
gagttcgtga ccgccgccgg gattacacat ggcatggacg agctgtacaa gtaa           594
```

<210> SEQ ID NO 27
<211> LENGTH: 939
<212> TYPE: DNA
<213> ORGANISM: Artificial sequence
<220> FEATURE:
<223> OTHER INFORMATION: Synthetic nucleotide sequence

<400> SEQUENCE: 27

```
atgtcgcgga cccggctccc ttccccaccc gcacccagcc cagcgttttc ggccgactcg      60
ttctcagacc tgcttaggca gttcgacccc tcactgttta acacatcgtt gttcgactcc     120
cttcctccgt ttggggcgca ccatacgag gcggccaccg gggagtggga tgaggtgcag      180
tcgggattga gagctgcgga tgcaccaccc ccaaccatgc gggtggccgt caccgctgcc     240
cgaccgccga gggcgaagcc cgcaccaagg cggagggcag cgcaaccgtc cgacgcaagc     300
cccgcagcgc aagtagattt gagaactttg ggatattcac agcagcagca ggaaaagatc     360
aagcccaaag tgaggtcgac agtcgcgcag catcacgaag cgctggtggg tcatgggttt     420
acacatgccc acatcgtagc cttgtcgcag caccctgcag cccttggcac ggtcgccgtc     480
aagtaccagg acatgattgc ggcgttgccg gaagccacac atgaggcgat cgtcggtgtg     540
gggaaacagt ggagcggagc ccgagcgctt gaggccctgt tgacggtcgc gggagagctg     600
agagggcctc cccttcagct ggacacgggc cagttgctga agatcgcgaa gcggggagga     660
gtcacggcgg tcgaggcggt gcacgcgtgg cgcaatgcgc tcacgggagc accctcaac     720
ctgaccccag agcaggtcgt ggcaatcgcc tccaacattg gcgggaaaca ggcactcgag     780
actgtccagc gcctgcttcc cgtgctgtgc aagcgcacg gactcacccc agagcaggtc     840
gtggcgatcg caagccacga cggaggaaag caagccttgg aaacagtaca gaggctgttg     900
cctgtgctgt gccaagcgca cggcctcacc ccagagcag                             939
```

<210> SEQ ID NO 28
<211> LENGTH: 138
<212> TYPE: DNA
<213> ORGANISM: Artificial sequence
<220> FEATURE:
<223> OTHER INFORMATION: Synthetic nucleotide sequence

<400> SEQUENCE: 28
gtcgtggcaa tcgcgagcaa taacggcgga aaacaggctt tggaaacggt gcagaggctc    60
cttccagtgc tgtgccaagc gcacggatta accccagagc aggtcgtggc aatcgcctcc   120
aacattggcg ggaaacag                                                 138

<210> SEQ ID NO 29
<211> LENGTH: 138
<212> TYPE: DNA
<213> ORGANISM: Artificial sequence
<220> FEATURE:
<223> OTHER INFORMATION: Synthetic nucleotide sequence

<400> SEQUENCE: 29
gtcgtggcaa tcgcgagcaa tggaggcgga aaacaggctt tggaaacggt gcagaggctc    60
cttccagtgc tgtgccaagc gcacggatta accccagagc aggtcgtggc aatcgcctcc   120
aacattggcg ggaaacag                                                 138

<210> SEQ ID NO 30
<211> LENGTH: 153
<212> TYPE: DNA
<213> ORGANISM: Artificial sequence
<220> FEATURE:
<223> OTHER INFORMATION: Synthetic nucleotide sequence

<400> SEQUENCE: 30
atgctggaga gcatgatcaa gaagccccgc cccactcggg ctgaaggcag tgatgtggcc    60
aatgcagtcc tggatggagc cgactgcatc atgctgtctg gagaaacagc caaagggac   120 tatcctctgg aggctgtgcg catgcagcac ctg                                153

<210> SEQ ID NO 31
<211> LENGTH: 167
<212> TYPE: DNA
<213> ORGANISM: Artificial sequence
<220> FEATURE:
<223> OTHER INFORMATION: Synthetic nucleotide sequence

<400> SEQUENCE: 31
atagctcgtg aggctgaggc agccatgttc caccgcaagc tgtttgaaga acttgtgcga    60
gcctcaagtc actccacaga cctcatggaa gccatggcca tgggcagcgt ggaggcttct   120
tataagtgtt tagcagcagc tttgatagtt ctgacggagt ctggcag                 167

<210> SEQ ID NO 32
<211> LENGTH: 167
<212> TYPE: DNA
<213> ORGANISM: Artificial sequence
<220> FEATURE:
<223> OTHER INFORMATION: Synthetic nucleotide sequence

<400> SEQUENCE: 32
attgcccgtg aggcagaggc tgccatctac cacttgcaat tatttgagga actccgccgc    60
ctggcgccca ttaccagcga ccccacagaa gccaccgccg tgggtgccgt ggaggcctcc   120
ttcaagtgct gcagtggggc cataatcgtc ctcaccaagt ctggcag                 167

<210> SEQ ID NO 33
<211> LENGTH: 184
<212> TYPE: DNA
<213> ORGANISM: Artificial sequence
<220> FEATURE:
<223> OTHER INFORMATION: Synthetic nucleotide sequence

<400> SEQUENCE: 33

```
gtctgctcac caggcggcca gataccgccc acgtgccccc atcattgctg tgacccggaa      60
tccccagaca gctcgtcagg cccacctgta ccgtggcatc ttccctgtgc tgtgcaagga     120
cccagtccag gaggcctggg ctgaggacgt ggacctccgg gtgaactttg ccatgaatgt     180
ttaa                                                                   184
```

<210> SEQ ID NO 34
<211> LENGTH: 165
<212> TYPE: DNA
<213> ORGANISM: Artificial sequence
<220> FEATURE:
<223> OTHER INFORMATION: Synthetic nucleotide sequence

<400> SEQUENCE: 34

```
atggctggac tgcctgcaaa tgcctccacg gtggtcggag gggacgtaga atttgtctgc      60
aaggtttata gtgatgccca gccccatatc cagtggatca acatgtgga aaagaacggc     120 agtaaatatg gacctgatgg gctgccctac ctcaaggtcc tgaag                     165
```

<210> SEQ ID NO 35
<211> LENGTH: 148
<212> TYPE: DNA
<213> ORGANISM: Artificial sequence
<220> FEATURE:
<223> OTHER INFORMATION: Synthetic nucleotide sequence

<400> SEQUENCE: 35

```
cactcgggga taaatagctc caatgcagaa gtgctggctc tgttcaatgt gacggagatg      60
gatgctgggg aatatatatg taaggtctcc aattatatag ggcaggccaa ccagtctgcc     120
tggctcactg tcctgcccaa acagcaag                                        148
```

<210> SEQ ID NO 36
<211> LENGTH: 145
<212> TYPE: DNA
<213> ORGANISM: Artificial sequence
<220> FEATURE:
<223> OTHER INFORMATION: Synthetic nucleotide sequence

<400> SEQUENCE: 36

```
gccgccggtg ttaacaccac ggacaaagaa attgaggttc tctatattcg gaatgtaact      60
tttgaggatg ctggggaata tacgtgcttg gcgggtaatt ctatcgggat atcctttcac     120
tctgcatggt tgacagttct gccag                                           145
```

<210> SEQ ID NO 37
<211> LENGTH: 182
<212> TYPE: DNA
<213> ORGANISM: Artificial sequence
<220> FEATURE:
<223> OTHER INFORMATION: Synthetic nucleotide sequence

<400> SEQUENCE: 37

```
cacctgtgag agagaaggag atcacagctt ccccagatta cctggagata gctatttact      60 gcatagggt cttcttaatc gcctgcatgg tggtgacagt catcttttgc cgaatgaaga     120
ccacgaccaa gaagccagac ttcagcagcc agccagctgt gcacaagctg accaagcgct     180
aa                                                                    182
```

```
<210> SEQ ID NO 38
<211> LENGTH: 774
<212> TYPE: DNA
<213> ORGANISM: Artificial sequence
<220> FEATURE:
<223> OTHER INFORMATION: Synthetic nucleotide sequence

<400> SEQUENCE: 38
gtctgcgtct accccaacc cccactgccc caactccgcg tcagtctctc agtccgggaa      60
cccgaactgg ctccctttcc ccatcctatc cccagcacag gatgtccagg ggcgcgcatt    120
taaaaaaaaa attaggagaa gaagctcgag agttagactg attctaactt ttctgtctcg    180
cctgaggacg cttgtggccc ttctctggct cccacggtcc gcgaagtcca ctggaattcc    240
ccgtaaagag gctcttgact cttaggattg gggatcagtt ttgaaagagg aagggagaaa    300
ggatacaagt tcccgggatg cctggaggga agggcggggg agcggggcaa ggattaagtc    360
ctaaggtgtc cgaagttctt tggaccttt ggttggggag agagagccct taagatggga     420
ttgaaaactt tgaagcgcac tgaattattt cctaagaaca aagatgggac agaatgggag    480
acacagacgg aaagctagcc aaacaagggc gtgtttcttc aatccctcaa gttggggacc    540
tgagcttgct gtcttcggcc gagcgtgtgg tcccggggtg gcgtggggtg ggggtggga    600 tgcgagatga gtcactgagt ggttccagct ctgggagaga gattacctag ggtcccttga    660
gccccaaagc agcgatccct tagccccagg accccagcca acctggcacc cgtttgttgt    720
gtgtctcaca cccggtccat gccggccgcc cgcgcccgct ctccgctgtc ccag          774

<210> SEQ ID NO 39
<211> LENGTH: 215
<212> TYPE: DNA
<213> ORGANISM: Artificial sequence
<220> FEATURE:
<223> OTHER INFORMATION: Synthetic nucleotide sequence

<400> SEQUENCE: 39
gtacccgggc gcgcggtgtg gcactgcaca cgaatggcta actttctctt tctctctccc     60
tccctgtctt tccctctctc tctctttccc gctgtccctg tcctttatgg tctacgcacc    120
ctcaacccgc accttgcggg atcacgctgc ctgctgcacc ccaccccctt ccccttcct    180 tccccccacc cccgtactcc actgccaact cccag                               215

<210> SEQ ID NO 40
<211> LENGTH: 504
<212> TYPE: DNA
<213> ORGANISM: Artificial sequence
<220> FEATURE:
<223> OTHER INFORMATION: Synthetic nucleotide sequence

<400> SEQUENCE: 40
gtaagtgcac gctcacactg cctccctcac cccctgaccg cgtggccgct ctggggtca      60 ccacaggggc tgcagagcaa aggaagaggg tgatcctcct cctacaggac acctgcacac    120
agcctggcca tagcccagag cactggatgc cgcctctgct gctgcgcaca tttcatttat    180
attctgtcct ttccccttttt tctcctcttc tttacctcct cccctttggt tggaggtggg    240
tgggtgagaa gctggggaac acggcctctg aaatggggac tgctggaagt gaacttcgcc    300
tcctgctggt ataaaaccgc tgaagtgtat gtcatcacca aggtctgtac aaaacagaat    360
ccctagtgtt cttgtttgcc accctacccc caaaaccccc ggtggttttc gctgatggac    420
```
ctagtctgag tgggttcaga gagcctgacc tttggaattc ctcactttct ccccatctct    480
gagtgtcttt catcctctgc ctag    504

<210> SEQ ID NO 41
<211> LENGTH: 114
<212> TYPE: DNA
<213> ORGANISM: Artificial sequence
<220> FEATURE:
<223> OTHER INFORMATION: Synthetic nucleotide sequence

<400> SEQUENCE: 41
gggacttctg cccgcctcct tcctgctcgt gtcaaaatga atggcgctcg gcgttgcgtg    60
gtacgttata ttccggccaa gcagccattc atgggagacg agataggcgg acac    114

<210> SEQ ID NO 42
<211> LENGTH: 115
<212> TYPE: DNA
<213> ORGANISM: Artificial sequence
<220> FEATURE:
<223> OTHER INFORMATION: Synthetic nucleotide sequence

<400> SEQUENCE: 42
gggacttctg cccgcctcct tccgctgagg actcggcacc gaatttgcca acgtctggtc    60
acgaccgtag tacactaccc ctcgaaatca cgagggagac gagataggcg gacac    115

<210> SEQ ID NO 43
<211> LENGTH: 114
<212> TYPE: DNA
<213> ORGANISM: Artificial sequence
<220> FEATURE:
<223> OTHER INFORMATION: Synthetic nucleotide sequence

<400> SEQUENCE: 43
gggacttctg cccgcctcct tccgcttacc ggacgcctta aggcatcagc atgcagtgct    60
tggtacgtta tattcagctg caactcggga tgcggagacg agataggcgg acac    114

<210> SEQ ID NO 44
<211> LENGTH: 33
<212> TYPE: DNA
<213> ORGANISM: Artificial sequence
<220> FEATURE:
<223> OTHER INFORMATION: Synthetic nucleotide sequence

<400> SEQUENCE: 44
ggtgatacca gccgaaaggc ccttggcagc acc    33

<210> SEQ ID NO 45
<211> LENGTH: 19
<212> TYPE: DNA
<213> ORGANISM: Artificial sequence
<220> FEATURE:
<223> OTHER INFORMATION: Synthetic nucleotide sequence

<400> SEQUENCE: 45
cgtacaccat cagggtacg    19

<210> SEQ ID NO 46
<211> LENGTH: 50
<212> TYPE: DNA
<213> ORGANISM: Artificial sequence
<220> FEATURE:
<223> OTHER INFORMATION: Synthetic nucleotide sequence

<400> SEQUENCE: 46
aggccgatct atggacgcta taggcacacc ggatacttta acgattggct     50

<210> SEQ ID NO 47
<211> LENGTH: 97
<212> TYPE: DNA
<213> ORGANISM: Artificial sequence
<220> FEATURE:
<223> OTHER INFORMATION: Synthetic nucleotide sequence

<400> SEQUENCE: 47
gctgtcaccg atgtgctttt ccggtctgat gagtccgttg tccataccag catcgtcttg     60
atgcccttgg cagggacggg acggaggacg aaacagc     97

<210> SEQ ID NO 48
<211> LENGTH: 115
<212> TYPE: DNA
<213> ORGANISM: Artificial sequence
<220> FEATURE:
<223> OTHER INFORMATION: Synthetic nucleotide sequence

<400> SEQUENCE: 48
gctgtcaccg atgtgctttt ccggtctgat gagtccgttg tccaaaacat accagatttc     60
gatctggaga ggtgaagaat tcgaccacct ggacgaggac ggaggacgaa acagc     115

<210> SEQ ID NO 49
<211> LENGTH: 2949
<212> TYPE: DNA
<213> ORGANISM: Artificial sequence
<220> FEATURE:
<223> OTHER INFORMATION: Synthetic nucleotide sequence

<400> SEQUENCE: 49
cgccaccatg gtgagcaagg gcgaggagct gttcaccggg gtggtgccca tcctggtcga     60
gctggacggc gacgtaaacg gccacaagtt cagcgtccgc ggcgagggcg agggcgatgc     120
caccaacggc aagctgaccc tgaagttcat ctgcaccacc ggcaagctgc ccgtgccctg     180
gcccaccctc gtgaccacct tcggctacgg cgtggcctgc ttcagccgct accccgacca     240
catgaagcag cacgacttct tcaagtccgc catgcccgaa ggctacgtcc aggagcgcac     300
catctctttc aaggacgacg gtacctacaa gacccgcgcc gaggtgaagt tcgagggcga     360
caccctggtg aaccgcatcg agctgaaggg catcgacttc aaggaggacg gcaacatcct     420
ggggcacaag ctggagtaca acttcaacag ccacaacgtc tatatcacgg ccgacaagca     480
gaagaacggc atcaaggcta acttcaagat ccgccacaac gttgaggacg gcagcgtgca     540
gctcgccgac cactaccagc agaacacccc catcggcgac ggccccgtgc tgctgcccga     600
caaccaccag gtctgcgtct accccaacc cccactgccc caactccgcg tcagtctctc     660
agtccgggaa cccgaactgg ctcccttcc ccatcctatc cccagcacag gatgtccagg     720
ggcgcgcatt taaaaaaaaa attaggagaa gaagctcgag agttagactg attctaactt     780
ttctgtctcg cctgaggacg cttgtggccc ttctctggct cccacggtcc gcgaagtcca     840
ctggaattcc ccgtaaagag gctcttgact cttaggattg gggatcagtt ttgaaagagg     900
aagggagaaa ggatacaagt tcccgggatg cctggaggga agggcggggg agcggggcaa     960
ggattaagtc ctaaggtgtc cgaagttctt tggaccttttt ggttggggag agagagccct     1020
taagatggga ttgaaaactt tgaagcgcac tgaattattt cctaagaaca agatgggac     1080 agaatgggag acacagacgg aaagctagcc aaacaagggc gtgtttcttc aatccctcaa     1140

-continued

```
gttggggacc tgagcttgct gtcttcggcc gagcgtgtgg tcccggggtg gcgtggggtg    1200 ggggggtggga tgcgagatga gtcactgagt ggttccagct ctgggagaga gattacctag   1260
ggtcccttga gccccaaagc agcgatccct tagcccagg accccagcca acctggcacc     1320
cgtttgttgt gtgtctcaca cccggtccat gccggccgcc cgcgcccgct ctccgctgtc    1380
ccagctcgtg agcaagggcg aggaggataa catggccatc atcaaggagt tcatgcgctt    1440
caaagtgcac atggagggct ccgtgaacgg ccacgagttc gagatcgagg gcaaggtacc    1500
cgggcgcgcg gtgtggcact gcacacgaat ggctaactt ctctttctct ctccctccct    1560
gtctttccct ctctctctct ttcccgctgt ccctgtcctt tatggtctac gcaccctcaa    1620 cccgcaccttt gcgggatcac gctgcctgct gcaccccacc cccttccccc ttccttcccc   1680 ccaccccgt actccactgc caactcccag ctgagccatc agtccgccct gagcaaagac     1740
cccaacgaga agcgcgatca catggtcctg ctggagttcg tgaccgccgc cgggattaca    1800
catggcatgg acgagctgta caaggatgta agtgcacgct cacactgcct ccctcacccc    1860
ctgaccgcgt ggccgctctg ggggtcacca caggggctgc agagcaaagg aagagggtga   1920
tcctcctcct acaggacacc tgcacacagc ctggccatag cccagagcac tggatgccgc    1980
ctctgctgct gcgcacattt catttatatt ctgtcctttc ccctttttct cctcttcttt   2040
acctcctccc ctttggttgg aggtgggtgg gtgagaagct ggggaacacg gcctctgaaa   2100
tggggactgc tggaagtgaa cttcgcctcc tgctggtata aaaccgctga agtgtatgtc   2160
atcaccaagg tctgtacaaa acagaatccc tagtgttctt gtttgccacc ctaccccaa   2220 aaccccggt ggttttcgct gatggaccta gtctgagtgg gttcagagag cctgacctt    2280 ggaattcctc actttctccc catctctgag tgtctttcat cctctgccta gggcgagggc   2340
cgcccctacg agggcaccca gaccgccaag ctgaaagtga ccaagggtgg cccctgccc   2400 ttcgcctggg acatcctgtc ccctcagttc atgtacggct ccaaggccta cgtgaagcac   2460
cccgccgaca tccccgacta cttgaagctg tccttccccg agggcttcaa gtgggagcgc   2520
gtgatgaact tcgaggacgg cggcgtggtg accgtgaccc aggactcctc cctgcaagac   2580
ggcgagttca tctacaaagt gaagctgcgc ggcaccaact tccctccga cggccccgta   2640 atgcagaaga agaccatggg ctgggaggcc tcctccgagc ggatgtaccc cgaggacggc   2700
gccctgaagg gcgagatcaa gcagaggctg aagctgaagg acggcggcca ctacgacgct   2760
gaagtcaaga ccacctacaa ggccaagaag cccgtgcagc tgcccggagc ctacaacgtc   2820
aacatcaagt tggacatcac ctcccacaac gaggactaca ccatcgtgga acagtacgaa   2880
cgcgccgagg gccgccactc caccggcggc atggacgagc tgtacaagta actgatcata   2940
agcggccgc                                                          2949
```

PROGRAMMABLE ALTERNATIVE SPLICING DEVICES AND USES THEREOF

CROSS-REFERENCING

This application claims the benefit of U.S. provisional application Ser. No. 62/101,921, filed on Jan. 9, 2015, which application is incorporated by reference herein.

GOVERNMENT RIGHTS

This invention was made with Government support under contract HR0011-11-2-0002 is awarded by the Defense Advanced Research Projects Agency. The Government has certain rights in the invention.

BACKGROUND

Certain aspects of the present invention generally relate to RNA molecules and the alternative splicing thereof. More specifically, certain aspects of the present invention describe precise exon selection in a multi-exon device.

Cells coordinate largely complex tasks, such as metabolic processes, differentiation, gene expression, and transport, by processing signals within the cellular environment or from external cues to elicit a specific genetic response. An average mammalian gene encodes approximately three RNA transcripts, which can then be translated to generate distinct protein isoforms (Pan et al, Nature Genetics 2008, 40: 1413-1415). Typically natural proteins like densin, a LAP protein, modulate their usage of protein-protein interaction and localization domains to generate diverse and functionally distinct proteins with unique roles within their cellular networks (Jiao et al, J Neurochem 2008 105: 1746). While a number of engineered molecular platforms and devices for mammalian cells have been constructed, they are primarily limited to controlling gene expression, that is increasing or decreasing gene expression (i.e. turning a gene "ON" or "OFF") or modulating protein activity post-translationally once the protein isoform has been produced. Our ability to effectively engineer biological systems is limited by the tools and strategies available to detect, transmit, and so control molecular information. Devices that support more sophisticated control, such as control of spatial organization or protein function, are needed to advance the scale and complexity with which mammalian devices can be designed and integrated within native cellular networks.

RNA-based control devices have been previously developed to process biomolecular inputs and produce regulated protein outputs (Liang et al Mol Cell 2011 43: 915-926; Culler et al. Science 2010 330: 1251-1255). RNA exhibits unique advantages as a substrate for genetic device design because RNA structures can be designed with relative ease and RNA exhibits diverse sensing and regulatory activities. In one example, RNA devices based on an alternative splicing mechanism linked disease biomarkers to cell death by modulating the inclusion of a premature stop codon in a suicide gene (Culler et al, Science 2010 330: 1251-1255). Alternative splicing, a prevalent post-transcriptional regulatory mechanism, is a process by which multiple protein isoforms are generated by altering the ways in which exons, or protein coding regions, are joined, and introns, or non-protein coding regions, are excised. While alternative splicing has the capacity to decompress information encoded in a single gene and modulate the usage of domains, this capability has not been harnessed in engineered molecular systems.

Studies performed using high-throughput sequencing technology estimate approximately 95% of human multi-exon genes undergo alternative splicing, with an average of three unique transcripts encoded per gene (Pan et al, Nature Genetics 2008 40: 1413-1415). In this manner, alternative splicing is critical for increasing protein diversity in natural systems. Yet prior studies have largely focused on linking alternative splicing events to turning "ON" or "OFF" gene expression, rather than increasing protein diversity in the cell. Such designs have modulated exon skipping to modulate the inclusion of a premature stop codon (Culler et al, Science 2010 330: 1251-1255), the incorporation of frameshift mutations to decide which one of two genes downstream of the final exon is translated (Newman RNA 2006 12: 1129-1141), and intron excision in response to small molecule binding (Kim et al BMC Mol Biol 2008 9: 23). While these constructs depend on an alternative splicing event for the output, they are largely limited to controlling gene expression in the context of simple alternative splicing modes or affecting the translation of the mRNA molecule that is generated.

SUMMARY

Provided herein, among other things, is an alternative splicing device with an intron framework that produces predictable splicing events when placed in the context of different exon sequences. An engineered intron framework allows for exons to be swapped in and out. The ability to recode exons enables the modular and extensible implementation of this device. A gene can be split into artificial exons that encode precise functions using specific design rules and introduced into the intron framework. The sequence space available in the intronic regions is used to design an intron framework that implements alternatively spliced events, specifically the mutually exclusive inclusion of exons. The regulatory components necessary to enforce splicing events are placed within the introns, or non-protein coding regions, such that these elements are decoupled from the exon sequence and do not disrupt the proteins encoded by the device. This is critically important in maintaining the ability to readily swap exon sequences in the alternative splicing device. The alternative splicing device can sense various intracellular and extracellular signals and precisely combine modular exons in a regulated manner to increase protein diversity. By controlling how and in what combination exons are joined, numerous proteins can be created. More mutually exclusive exons can be added into the device to expand the number of protein isoforms that are encoded by the device.

An extension of the alternative splicing platform has the potential to broaden current regulatory capabilities by providing a strategy to dynamically program protein function. To control splicing, RNA control elements can be harnessed in natural and synthetic systems to modulate splicing efficiency and splice site choice through RNA structural responses to or sequence obstruction by small molecule, protein, or oligonucleotide binding (Culler et al, Science 2010 330 1251-1255 and Kim et al BMC Mol Biol 2008 9: 23). Described herein are alternative splicing devices in which exons can be readily recoded so any gene can be programmed in response to intracellular or extracellular signals to produce the protein variant required by the cell. These novel devices enable compressing information for many protein isoforms, recoding exons sequences within an engineered intron framework, and precisely altering splicing patterns using RNA switches to program protein function and elicit a cellular response. This invention will be applied for constructing modular and extensible alternative splicing devices that can integrate with native mammalian pathways or be utilized to build synthetic pathways and produce diverse protein variants in a controlled manner.

The alternative splicing device platform technology can be used in a variety of applications where functionality beyond turning a gene "ON" or "OFF" is required, such as modulating enzymatic activities, protein-protein interactions, protein-DNA interactions, protein translocation, catalysis, and regulation, to ultimately engineer complex networks in mammalian organisms. Genes from various cellular processes can be incorporated into the alternative splicing device. The device can then be used to program proteins involved in a variety of applications, such as gene control, signal transduction, metabolism, subcellular localization, imaging applications, and correcting aberrant splicing patterns. For gene control, modular transcription factors, such as transcription activator-like effector (TALE) transcription factors, can be programmed by placing segments of the DNA binding domains or the effector domains (i.e., activator domains, repressor domains, etc.) into mutually exclusive exons within the device to modify gene expression. In signal transduction cascades, enzymes (e.g., protein kinase C) involved in controlling the activation of other proteins can trigger a biochemical chain of events inside the cell. By altering the catalytic or regulatory domains of these enzymes, the signal can be altered or amplified to change the cell's response. In metabolic pathways, by altering the enzyme's regulatory domain (i.e., pyruvate kinase), the cell can control whether the enzyme is always active or if it can only function under specific conditions, such as the presence of a cofactor. For subcellular localization, protein isoforms (e.g. protein phosphatase-1) can be targeted to distinct and independent sites in the cell (i.e., nucleus or cytoplasm) permitting unique roles for each of the isoforms in regulating discrete cellular processes. For imaging applications, the development of fluorescent protein designs with novel characteristics facilitates the visualization of structural organization and dynamic processes in living cells. In the case of correcting aberrant splicing patterns, a number of diseases are caused by splicing mutations associated with changes in the relative levels of alternatively spliced isoforms, such as certain muscular dystrophies and some breast and ovarian cancers. By incorporating these incorrectly spliced genes into an alternative splicing device, the mutations can be removed while maintaining isoform profile production from a singular device. Thus novel platform technologies like this one that facilitate expressing related, yet distinct genetic information in a regulated manner have widespread applications in basic research, biotechnology, and medicine.

In certain embodiments, the device comprises an RNA capable of undergoing alternative splicing. Among other things, the RNA may comprise a first exon, a second exon, a third exon and a fourth exon, wherein the RNA is capable of being spliced into; i. a first splicing product comprising the second exon (i.e., a product that contains the first, second and fourth exons) or ii. a splicing second product comprising the third exon (i.e., a product that contains the first, third and fourth exons), wherein: i. an intron of the RNA, e.g., the intron between the first and second exons of the RNA, the intron between the second and third exons of the RNA or the intron between the third and fourth exons of the RNA, comprises an aptamer and ii. binding of a ligand to the aptamer determines whether the RNA is spliced into the first splicing product or the second splicing product. As would be understood from this disclosure, the first and second products contain either the second exon or the third exon, but not both exons (i.e., the exons are "mutually exclusive").

In this context, of a population of RNA molecules of a given design, the term "capable of" is intended to mean that at least 1% (e.g., at least 1%, at least 5%, at least 10%, at least 25%, at least 50%, at least 50%, at least 80%, at least 90%, or at least 95%) of the RNA molecules will be spliced into the desired product. Additional splicing products may be produced that contain the second or third exons, or fragments thereof, and fragments of intervening introns.

In any embodiments, the aptamer may be within 200 bases (e.g., within 100 bases, or within 50 bases) of a sequence that regulates splicing of the intron between the first and second exons. The aptamer may be in the intron between the first and second exons, the intron between the second and third exons, or the intron between the third and fourth exons. If the aptamer binds to a small molecule (e.g., a molecule of under 500 Da) the aptamer may be less than 50 bases from the splicing regulator sequence. If the aptamer binds to a protein, the aptamer may be less than 100 or 200 bases from the splicing regulator sequence. In some embodiments, in the intron between the second and third exons, the 5' splice junction is less than 50 nucleotides from the branch point sequence, which makes splicing mutually exclusive. In any embodiment, the RNA may comprise one or more further exons in addition to the first, second, third and fourth exons. In some cases, the one or more further exons are 5' of the first exon, between the third and fourth exons, and/or 3' of the fourth exon.

The ligand for the aptamer may be a small molecule, a protein or a nucleic acid for example.

In any embodiment, one or more of the intron/exon junctions may comprise an insulator. In any embodiment, both ends of an intron may contain an insulator and, in certain embodiments, both ends of all of the introns may contain an insulator.

The first and second splicing products may encode different proteins, e.g., different transcription factors, different enzymes, different reporter proteins (e.g., different fluorescent proteins), etc.

In any embodiments, the RNA may comprise a ligand-activatable ribozyme that degrades the RNA in the presence of a second ligand.

Also provided is a eukaryotic cell (e.g., a mammalian cell) comprising a construct comprising a promoter, a transcribed region and a terminator, wherein the transcribed region is transcribed in the cell to produce the RNA of claim 1. In any embodiment, the eukaryotic cell may be present in a multicellular animal (i.e., in vivo) or in a cultured cell (i.e., in vitro).

Various methods for altering splicing in a cell are provided. In some embodiments, this method may comprise: in a eukaryotic cell, inducing contact between an RNA of the invention with the ligand for the aptamer, thereby altering the ratio of the first splicing product and the second splicing product.

In some embodiments, the ligand is added exogenously to the cell and in other embodiments the ligand may be generated endogenously within the cell.

In some embodiments the first splicing product and the second splicing product may encode different fluorescent proteins and the method comprises detecting expression of the different fluorescent proteins by the cell. In these embodiments, the cell may be present in a multicellular organism and the detecting is done in vivo.

In other embodiments the first splicing product and the second splicing product may encode different transcription factors. Addition of the ligand changes transcription within the cell.

The RNA advances capabilities of currently available tools and methods to engineer mammalian cells by providing a simple, controlled way to modulate protein domains and program the version of the protein required by the cellular context. For example, the system may be used to manipulate enzymatic activities or protein-protein interactions.

All patents and publications, including all sequences disclosed within such patents and publications, referred to herein are expressly incorporated by reference.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION OF EXEMPLARY EMBODIMENTS

The following description is not intended to limit the invention to any particular embodiment, but rather to enable any person skilled in the art to make and use this invention.

In some embodiments the alternative splicing device is an RNA molecule with an input module composed of a control element integrated near a regulatory sequence element and an output module composed of mutually exclusive protein coding sequences, or exons, which b encode variable internal protein sequence and are nested within external coding sequences, that can undergo alternative splicing. Upon activation of the input module, the state of the regulatory sequence element is altered to change the alternative splicing pattern and select a mutually exclusive exon that differs from default and produces a distinct protein isoform (FIG. 1A).

In some embodiments, the regulatory sequences include 5' splice sites, 3' splice sites, branch point sequences, polypyrimidine tracts, exonic splicing enhancers, exonic splicing silencers, intronic splicing enhancers, and intronic splicing silencers. The 5' splice site includes the consensus AG*GU sequence (where AG is in the exon, GU is in the intron, and * represents the exon-intron junction), the 3' splice site includes the consensus AG*G sequence (where AG is in the intron, G is in the exon, and * represents the intron-exon junction), the branch point sequence contains a conserved adenine ribonucleotide required for splicing, and the polypyrimidine tract (PPT) is comprised of a 1-50 nucleotide region with C and U ribonucleotides (FIG. 1B). In some cases the 5' splice site and 3' splice sites can differ from the consensus sequence. The enhancers and/or silencers may or may not be located completely within an intron sequence and can be partly or entirely within an exon sequence. Other sequences that potentially affect alternative splicing patterns are also within the scope of the regulatory sequence.

Figure 2:
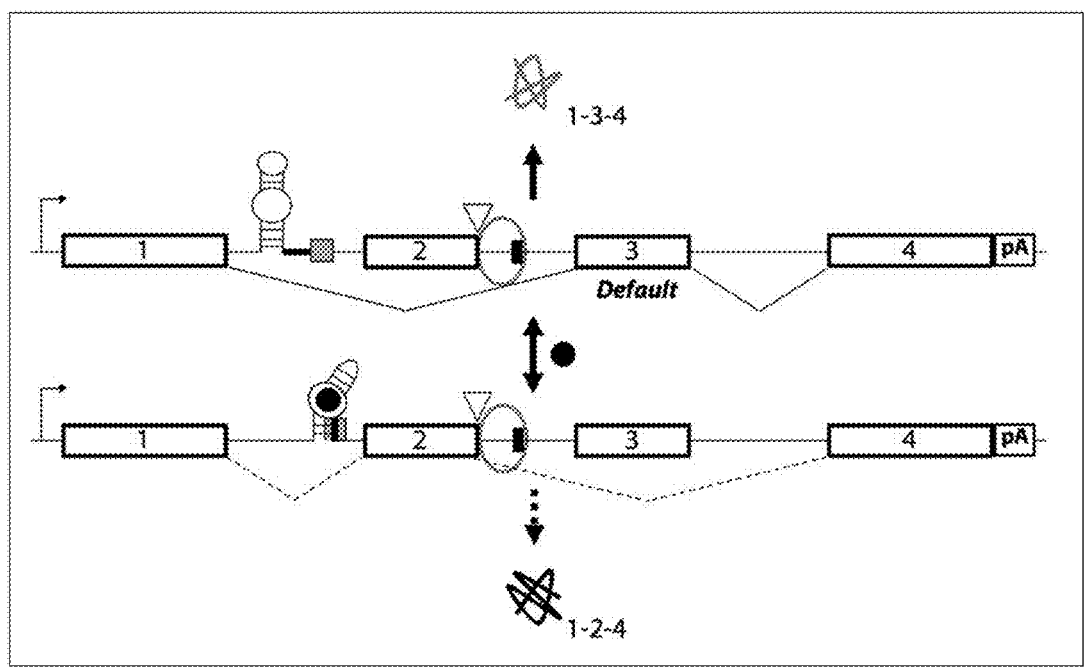
FIG. 2 schematically illustrates sequence elements enforce mutually exclusive splicing events in alternative splicing device.

The input module functions to detect the cellular environment and modulate the accessibility of an essential regulatory element. In some embodiments, the control element is a small molecule aptamer that is integrated within the intronic sequence adjacent to a regulatory sequence element. The aptamer is unstructured in its native state and the adjacent regulatory element is accessible by spliceosomal machinery within the cell. In its bound state, the aptamer binds its cognate small molecule with high affinity without assistance of any other factor and the aptamer undergoes a conformational change or rearrangement that physically occludes the accessibility of the regulatory element (FIG. 2). The aptamer can be an engineered folinic acid or theophylline aptamer but may alternatively be derived from any source, including but not limited to natural, artificial, engineered, selected, evolved or derived aptamers or aptamer domains. Small molecule aptamer binding is preserved under the conditions that support the alternative splicing function and should not affect the splicing of a RNA device that does not contain its cognate aptamer.

In certain embodiments, a linker sequence is introduced between the small molecule aptamer and the regulatory sequence element. The linker sequence can be 5-50 nt, in length comprised on any of combination of "A," "T," "C," "G," and can be designed or evolved to allow for switching between two structural folds (FIG. 2). One fold will leave the regulatory sequence element accessible while it is hidden in the other. Small molecule binding drives so switching between the two structural states. The small molecule aptamer can be an engineered folinic acid or theophylline aptamer but may alternatively be derived from any source, including but not limited to natural, artificial, engineered, selected, evolved or derived aptamers or aptamer domains. Small molecule aptamer binding is preserved under the conditions that support the alternative splicing function and should not affect the splicing of a RNA device that does not contain its cognate aptamer.

In certain embodiments, the small molecule is exogenous to a cell. For example, the small molecule may be exogenously added to an environment in which the cell resides, including but not limited to a cell culture plate or an in vivo environment. Alternatively, the small molecule could be synthesized and produced endogenously in a cell in the presence or to absence of an environmental stimuli or a change in cellular state.

In certain embodiments, the small molecule aptamer can be replaced by a protein aptamer. The protein aptamer would be similarly integrated near a regulatory sequence element in the intronic sequence. While an input module with a small molecule aptamer functions by controlling the accessibility of a regulatory element, proteins that bind to protein aptamers themselves interact with the spliceosomal machinery to alter how the spliceosome assembles on the device. Therefore, a protein aptamer can be readily incorporated at a greater number of integration sites within a range of ribonucleotides near the regulatory sequence element. The protein aptamer can be derived from any source, including but not limited to natural, artificial, engineered, selected, evolved or derived aptamers or aptamer domain. Protein aptamer binding is preserved under the conditions that support the alternative splicing function and should not affect the splicing of a RNA device that does not contain its cognate aptamer. In certain embodiments, the protein is exogenous to a cell. For example, the protein may be exogenously added to an environment in which the cell resides, including but not limited to a cell culture plate or an in vivo environment. Alternatively, the protein could be synthesized and produced endogenously in a cell in the presence or absence of an environmental stimuli or a change in cellular state. In these embodiments, the cell may be engineered to heterologous express the protein.

In certain embodiments, RNA or DNA oligonucleotides are exogenously added or produced endogenously to bind at, near, or far from the regulatory sequence element. Upon so binding, the oligonucleotides can block the regulatory sequence element itself or the sequence of another element that modifies the ability of the spliceosome to effectively assemble and facilitate the splicing event. In certain cases, the oligonucleotides may contain modified nucleotides and/or sugar-phosphate backbone.

The output module is comprised of a set of exons with interspaced intronic sequences capable of undergoing mutually exclusive splicing. In an example, an output module comprised of a first exon, a first intron, a second exon, a second intron, a third exon, and third intron, and a fourth exon encodes two different protein products, where the inclusion of the second or the third exon alters the identity and/or function of the product encoded by the coding sequence. Here the second and third exons are mutually exclusive and the first and fourth exons are always incorporated.

In certain embodiments, additional mutually exclusive exons and introns can be added into the alternative splicing device to increase the number of exons available for selection and increase the number of protein isoforms encoded by the device (FIG. 1C).

All exons in the output module have variable sequence and can be readily recoded or swapped in and out of the intron framework. In some embodiments, protein coding sequences are segmented into artificial exons with defined functions that are incorporated into an intron framework that enforces mutually exclusive alternative splicing.

Novel engineered insulator sequences are integrated at the exon-intron junctions within the intron framework of this RNA device to separate the protein coding sequence from the intronic sequence and decouple the regulatory elements from the protein coding sequence. The insulator elements maintain the identity of the junctions, promote proper exon recognition, and limit crosstalk between the input module and the output module. Examples of insulator sequences include, but are not limited to, those listed here (TABLE 1). The insulator elements can contain the 5' splice site and 3' splice site, but may also contain exonic splicing enhancers, exonic splicing silencers, intronic splicing enhancers, and intronic splicing silencers. Other sequences that potentially affect alternative splicing patterns are also within the scope of being included in an insulator sequence.

A number of sequence elements have been engineered within the alternative splicing devices to exhibit specific behavior. A few examples of sequence elements that have been tested are included here, and these include 5' splice sites, 3' splice sites, branch point sequences, polypyrimidine tracts, insulator sequences, and exon sizing sequences. 5' splice sites, 3' splice sites, branch point sequences, and polypyrimidine tracts are elements required by the splicing machinery for spliceosomal assembly. The insulator elements maintain the identity of the junctions, promote proper exon recognition, and limit crosstalk between the input module and the output module. The exon sizing sequences were used to vary the length of the mutually exclusive exons to assess exon size flexibility.

The mutually exclusive nature of the output module is enforced by the relative strength of regulatory elements associated with each of the mutually exclusive exons. The relative strength of a regulatory element is noted by its ability to recruit endogenous proteins that activate or repress the assembly of the spliceosomal machinery on the RNA device, thus facilitating the splicing function. In the example, the relative strengths of the polypyrimidine tracts associated with the second and third exons in a four exon-three intron system are major determinants in specifying the default pattern, with the relative branch point sequence strength playing a secondary role. The regulatory element that strictly enforces mutually exclusive behavior can be the polypyrimidine tract or the branch point sequence, but may alternatively be a 5' splice site, 3' splice site, an exonic splicing enhancer, an exonic splicing silencer, an intronic splicing enhancer, or an intronic splicing silencer. The enforced incompatibility of mutually exclusive exons sets one mutually exclusive product as the default state.

In certain embodiments, a physical constraint that limits or extends the relative distance between two or more regulatory sequence elements enforces mutually exclusive behavior. As an example, a distance shorter than 50 nucleotides between the second exon's 5' splice site and the third exon's branch point sequence inhibits proper spliceosomal machinery assembly and renders the middle two exons incompatible (FIG. 2). In this situation, the physical constraint prevents double inclusion of the mutually exclusive exons and the output module splices to only include one mutually exclusive exon.

In certain embodiments, the sequence capable of undergoing mutually exclusive alternative splicing is a segment of a natural gene. Intronic sequences can be sourced from genes including, but not limited to, the fibroblast growth factor receptor 2 genes (Newman et al RNA 2006 12: 1129-1141), alpha-tropomyosin genes (Gromak et al EMBO J 2003 22: 6356-6364), or pyruvate kinase genes (Chen et al, Nat Struct Mol Biol 2012 19: 346-354) in *Homo sapiens* or *Mus musculus*, and can be used to construct an output module with exons that are selected in a mutually exclusive manner.

Figure 11:
FIG. 11 shows the effect on splicing outcome from targeted modifications to alternative splicing regulatory sequence elements.
Figure 11:
Figure 11:
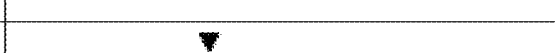
Figure 11:
Figure 11:
Figure 11:
Figure 11:
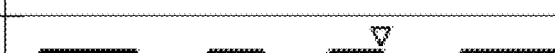
Figure 11:
Figure 11:
Figure 11:
Figure 11:
Figure 11:
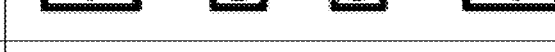
Figure 11:
Figure 11:
Figure 11:
Figure 11:
Figure 11:
Figure 11:
Figure 11:
Figure 11:
Figure 11:
Figure 11:
Figure 11:
Figure 11:
Figure 11:
Figure 11:
Figure 11:
Figure 11:
Figure 11:
Figure 11:
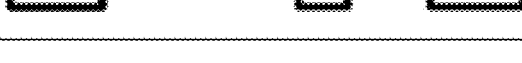

In certain embodiments, regulatory sequence elements can be tuned to alter the behavior of the alternative splicing device. Such changes can effect the incompatibility of mutually exclusive exons, change the default state of the device, eliminate the requirement of another regulatory sequence element, or strengthen the role of a particular regulatory sequence element. Regulatory sequence elements, including but not limited to 5' splice sites, 3' splice sites, branch point sequences, polypyrimidine tracts, exonic splicing enhancers, exonic splicing silencers, intronic splicing enhancers, and intronic splicing silencers, can be truncated, added, mutated, replaced, or incorporated in novel combinations to weaken, strengthen, or alter the device's performance (FIG. 11). For example, mutating the branch point to weaken it or replacing the branchpoint sequence with a stronger one to strengthen it tunes the branch point sequence regulatory element. In another example, a polypyrimidine tract can be modified by altering its nucleotide sequence or truncating its size. Novel sequences for 5' splice sites, 3' splice sites, branch point sequences, polypyrimidine tracts, exonic splicing enhancers, exonic splicing silencers, intronic splicing enhancers, and intronic splicing silencers could encompass, but are not limited to, those listed here (TABLE 1).

The mutually exclusive exons are incorporated into a final protein sequence where the first and last exons are always included in the different protein products. The functionality encoded within the mutually exclusive exons is distinct, modular, and interchangeable, in the form of protein domains, such that the incorporation of any of the exons results in a functional protein product. Protein domains may be a given protein sequence and structure that can function, exist, and evolve independently of the rest of the protein sequence, but alternatively can be any protein sequence that contains a part of or an entire function that is locally encoded and stable within the protein sequence. Examples of functions that can be encoded as protein domains within mutually exclusive exons and readily swapped to alter protein function or activity include, but are not limited to, DNA binding domains, protein-protein interaction domains, localization domains, effector domains, and regulatory domains.

In certain embodiment, the profile of protein isoforms can be tuned to produce multiple isoforms at the same time. In an example, with the four exon-three intron system that exhibits mutually exclusive splicing, the levels of isoform 1 can be X % in a range from 0-100% while the levels of isoform 2 can range from 0% to 100–X %. In this manner, the device programs outputs that are not just mutually exclusive, but outputs where variable levels of both isoforms, either isoform, or neither isoform can be produced. For example, in the four exon-three intron system, the two isoforms produced are isoform 1-2-4 and isoform 1-3-4. In certain embodiments, untranslated splicing variants can include isoform 1-4, isoform 1-2-3-4, and various additional isoforms that contain some combination of entire or segments of exons and introns. Such protein isoform profiles would also be present in alternative splicing devices with additional mutually exclusive exons.

The length of the mutually exclusive exons is variable and can vary from 50-250 nucleotides, but is not limited to this range. Exon sizing sequences can be added to the mutually exclusive exons to alter size (TABLE 1). The first and last exons in the device have no limitations on length.

The intron sequences surrounding the exons can be lengthened to introduce regulatory sequences or truncated to remove regulatory elements or decrease the size of the device. Intron sizes for each intron can range from 100-1000 nucleotides, but are not limited to this range.

In certain embodiments, a self-cleaving ribozyme (e.g., a hammerhead ribozyme) can be incorporated into any intron in the intron framework to degrade the device in the absence or presence of an intracellular or extracellular small molecule, protein, and/or DNA and RNA oligonucleotides.

In certain embodiments, the last exon in the output module does not encode a functional protein domain and it may be excluded or conditionally excluded in the protein product.

In certain embodiments, the second or third exon may comprise a sequence element that inhibits the expression of a product encoded by that mutually exclusive coding sequence, such as a translation stop codon, a transcription terminator, a secondary structure that inhibits ribosome function (e.g., scanning), a targeting miRNA (e.g., miRNA processing), or a self-cleaving ribozyme (e.g., a hammerhead ribozyme).

In certain embodiments, targeted changes can be made to the exon sequences within the alternative splicing device to mutate or remove cryptic splice site elements that prevent proper recognition of the defined exon-intron junctions within the alternative splicing device.

Applications in In Vivo Imaging

Alternative splicing devices that program fluorescent protein expression for in vivo imaging are described below.

The development of fluorescent protein designs with novel characteristics facilitates the visualization of structural organization and dynamic processes in living cells. Devices that can sense intracellular or extracellular signals, process the signal within the context of a particular cell, and respond with a detectable output have utility in advanced in vivo imaging applications. Novel methods to detect and produce a variety of inputs and outputs are needed to obtain cellular and molecular information in vivo, particularly in cases where the behavior of cells is inextricably linked to their milieu, such as cancer. Prior alternative splicing constructs were primarily cell based assays for screening the presence of regulatory elements within that construct (Culler Science 2010 330: 1251-1255.6; Newman et al RNA 2006 12: 1129-1141). These constructs successfully identified and integrated regulators of splicing but were limited to one or two fluorescent outputs and responding to protein levels within the cell.

A singular device that can process a variety of classes of molecular inputs to produce multiple distinct outputs has the ability to serve as a multi-input, multi-output in vivo imaging device. The alternative splicing device can be utilized to program fluorescent protein expression for an in vivo imaging device. In this way, multiple fluorescent signals can be produced from the detection of intracellular or extracellular signals to produce distinct fluorescent protein outputs in response to the cellular context.

This alternative splicing device is an RNA molecule with an input module composed of a control element integrated near a regulatory sequence element and an output module composed of mutually exclusive protein coding sequences, or exons, which encode variable internal protein sequence that encode segments of fluorescent proteins and are nested within external coding sequences, that can undergo alternative splicing. Upon activation of the control element in the input module, the state of the regulatory sequence element is altered to change the alternative splicing pattern and select a mutually exclusive exon that differs from default to change the fluorescent output from the device.

The input module functions to detect the cellular environment and modulate the accessibility of an essential regulatory element. The control element can be a small molecule aptamer, protein aptamer, and/or DNA or RNA oligonucleotide binding site. The small molecule, protein, or DNA/RNA oligonucleotide can be added exogenously to the cell or generated endogenously within the cell.

The output module is comprised of a set of exons with interspaced intronic sequences capable of undergoing mutually exclusive splicing. In an example, an output module comprised of a first exon, a first intron, a second exon, a second intron, a third exon, and third intron, and a fourth exon that encode different fluorescent proteins. A fluorescent protein can be split into artificial exons, such that the insulator sequences can be integrated and required exons sizes maintained.

In one embodiment, two fluorescent proteins can be split into artificial exons and these exons can be incorporated into the four exon-three intron mutually exclusive splicing device. These exons are then incorporated into the intron framework such that the artificial exons for fluorescent protein 1 are used to recode exons one and three while the artificial exons for fluorescent protein 2 are used to recode exons two and four. In certain embodiments, the two fluorescent reporters are GFP (or its variant Clover, both GFP and Clover are denoted "GFP" in this document), a green fluorescent protein from Aequorea victoria, and mCherry, a red fluorescent protein from Discosoma sp. The two fluorescent proteins are split into artificial exons such that GFP is encoded by exon 1 (GFP exon 1) and exon 3 (GFP exon 2) in the intron framework. mCherry is encoded by exon 2 (mCherry exon 1) and exon 4 (mCherry exon 2) in the intron framework (FIG. 3A). This alternative splicing device splices to produce the dominant isoform 1-3-4 to express GFP (FIG. 4A). The minor product (isoform 1-2-4) express mCherry. In certain embodiments, Clover, a variant of GFP can be used.

In alternate embodiments, the incorporation strategy can also be reversed such that the artificial exons for fluorescent protein 1 are used to recode exons two and four while the artificial exons for fluorescent protein 2 are used to recode exons one and three. In this embodiment, mCherry is encoded by exon 1 (mCherry exon 1) and exon 3 (mCherry exon 2) in the intron framework. GFP is encoded by exon 2 (GFP exon 1) and exon 4 (GFP exon 2) in the intron framework (FIG. 3B). This alternative splicing device splices to produce the dominant isoform 1-3-4 to expresses mCherry (FIG. 4B). The minor product (isoform 1-2-4) expresses GFP.

In certain embodiments, additional mutually exclusive exons and introns can be added into the alternative splicing device to increase the number of exons available for selection and increase the number of fluorescent reporters encoded by the device. In these embodiments, exons 1 and 4 encode constant regions and the mutually exclusive exons encode segments that alter the properties of the fluorescent proteins.

Figure 5:
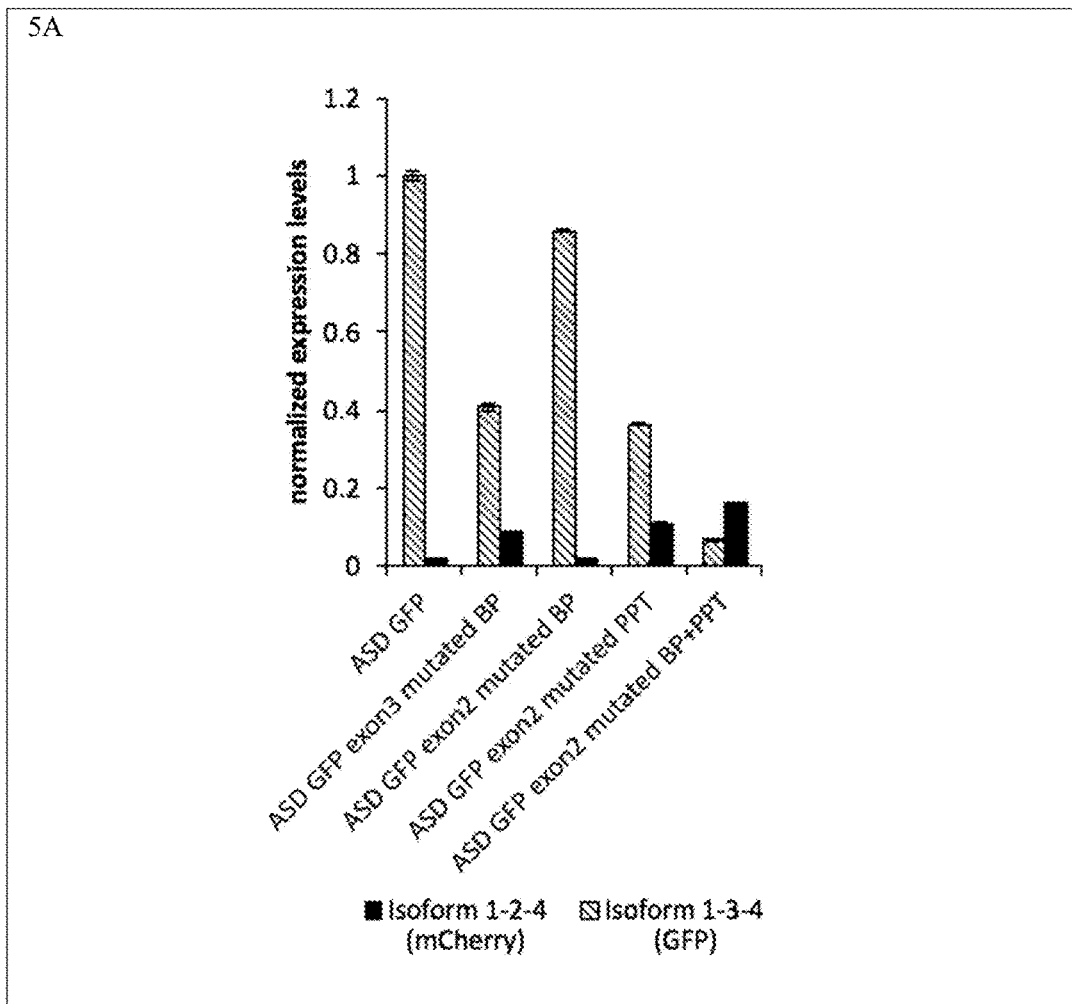
FIG. 5 shows the effect of various regulatory sequence elements in alternative splicing device (ASD) GFP.
Figure 5:
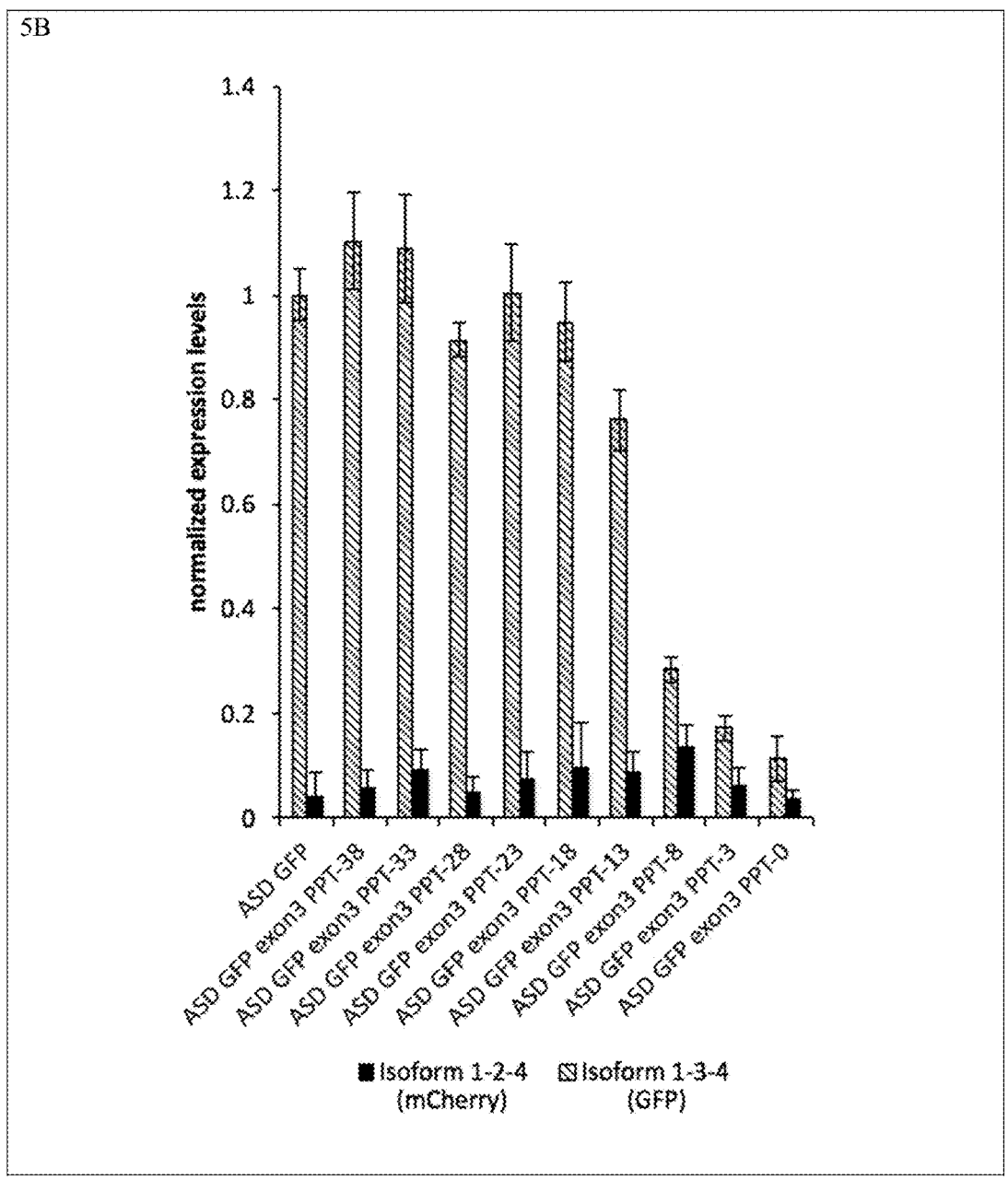
Figure 5:
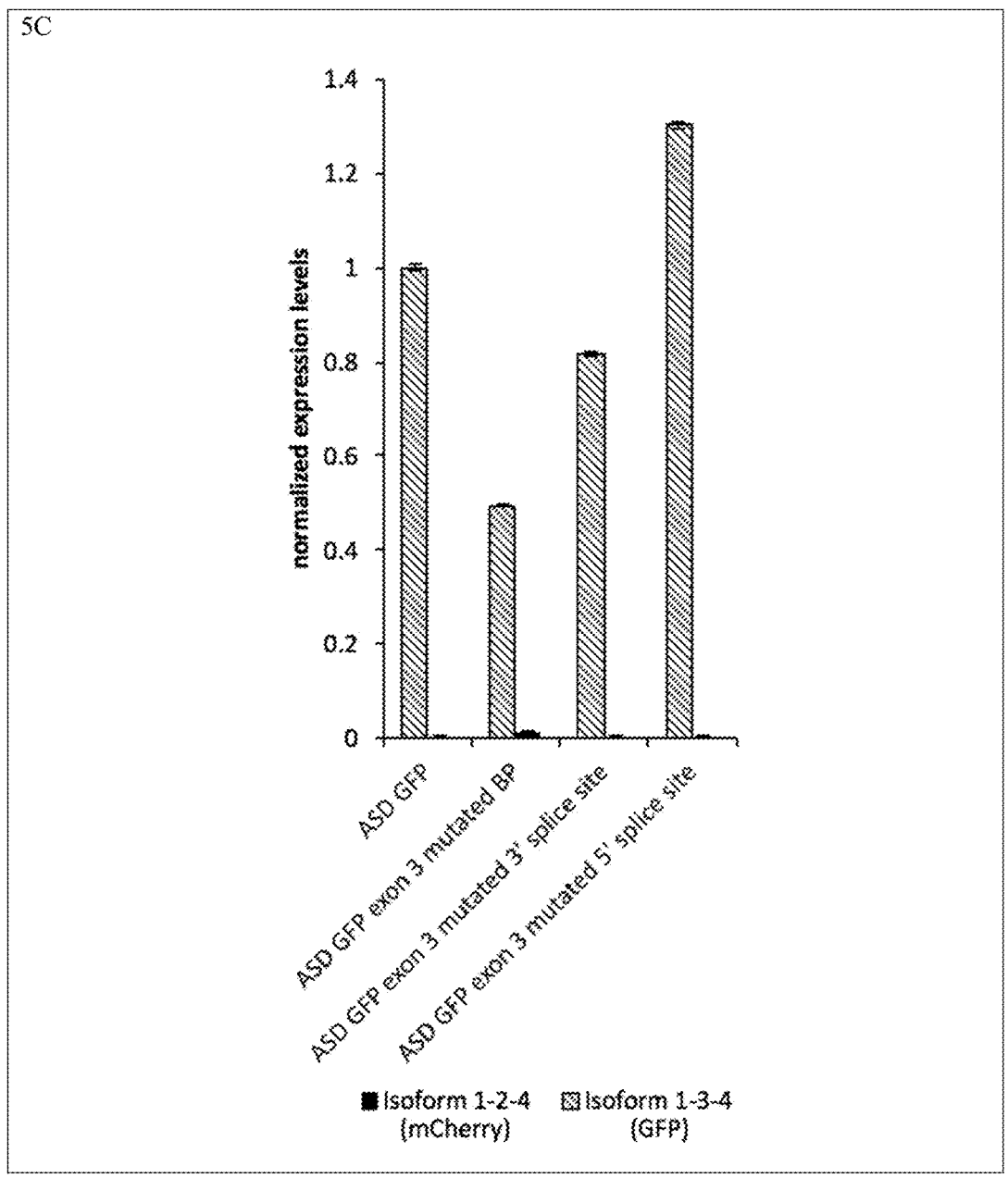
Figure 5:
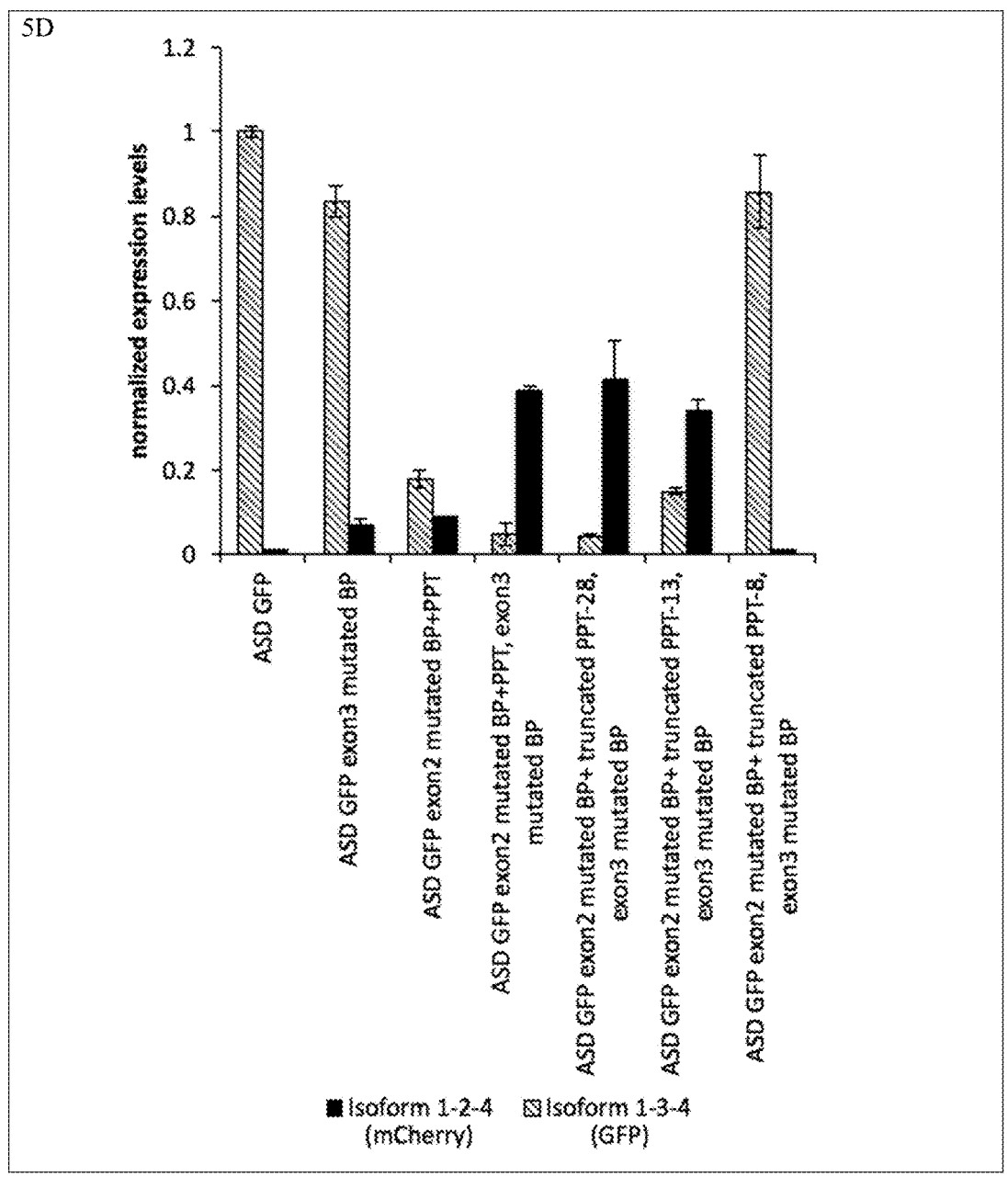

In certain embodiments, regulatory sequence elements can be tuned to alter the behavior of the alternative splicing device. Such changes can effect the incompatibility of mutually exclusive exons, change the default state of the device, eliminate the requirement of another regulatory sequence element, or strengthen the role of a particular regulatory sequence element. Regulatory sequence elements, including but not limited to 5' splice sites, 3' splice sites, branch point sequences, polypyrimidine tracts, intronic splicing enhancers, intronic splicing silencers, exonic splicing enhancers, and exonic splicing silencers, can be truncated, added, mutated, replaced, or incorporated in novel combinations to weaken, strengthen, or alter the device's performance. For example, mutating the branch point to weaken it or replacing the branchpoint sequence with a stronger one to strengthen it alters splicing patterns and thus the behavior of the device. In another example, a polypyrimidine tract can be modified by altering its nucleotide sequence or truncating its size (FIG. 5, 6).

Figure 7:
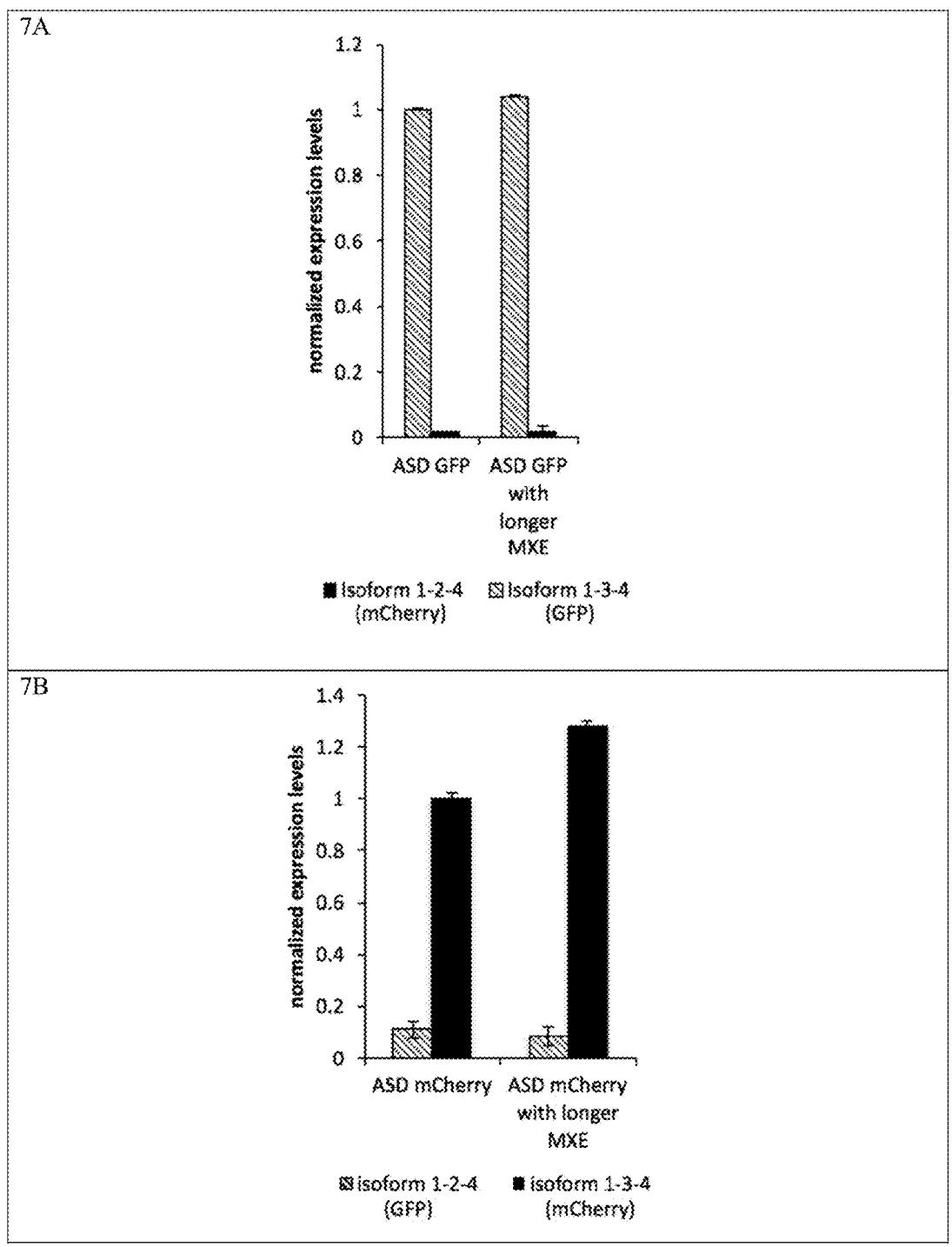
FIG. 7 shows the exon sizes within the two embodiments of alternative splicing devices that express fluorescent proteins.

The length of the mutually exclusive exons is variable and can vary from 50-250 nucleotides, but is not limited to this range. Exon sizing sequences can be added to the mutually exclusive exons to alter size (TABLE 1). The first and last exons in the device have no limitations on length (FIG. 7).

Figure 8:
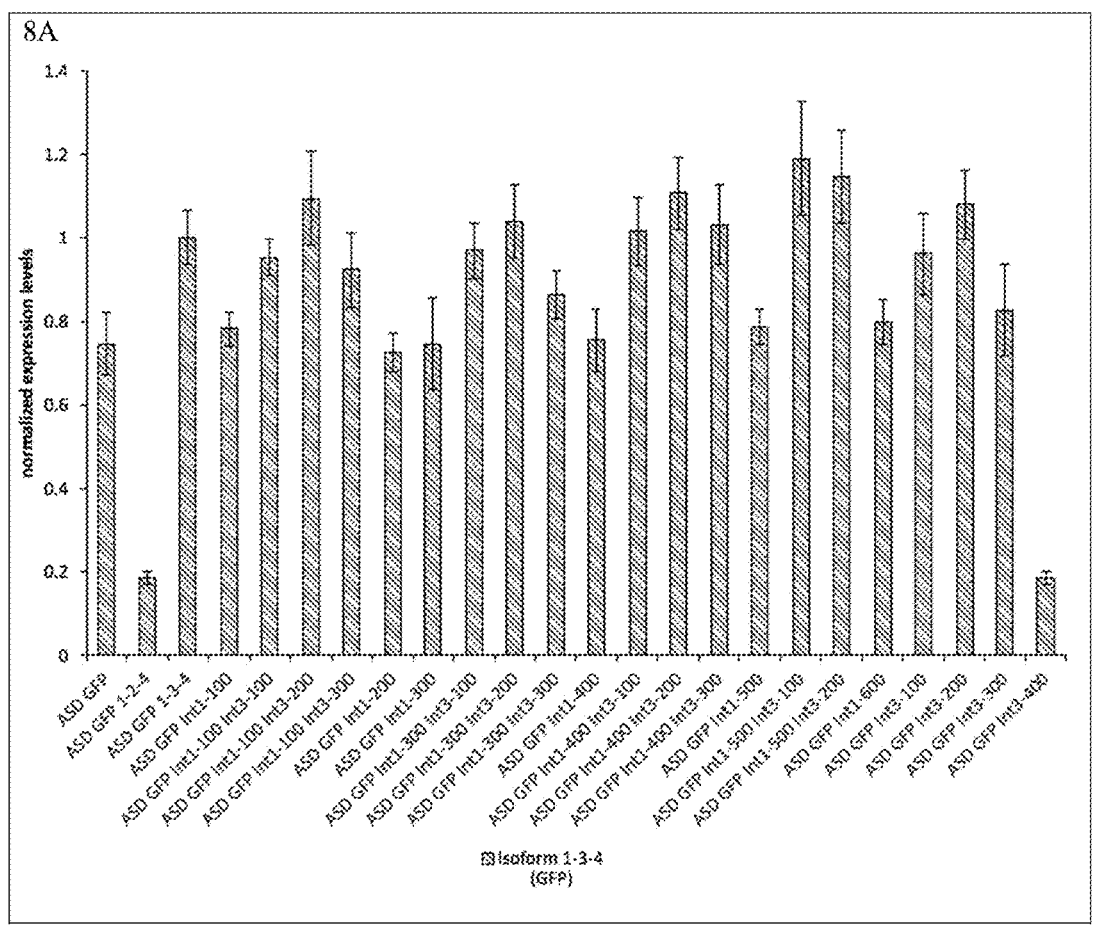
FIG. 8 shows the effect of varying intron sizes within the two embodiments of alternative splicing devices that express fluorescent proteins.
Figure 8:
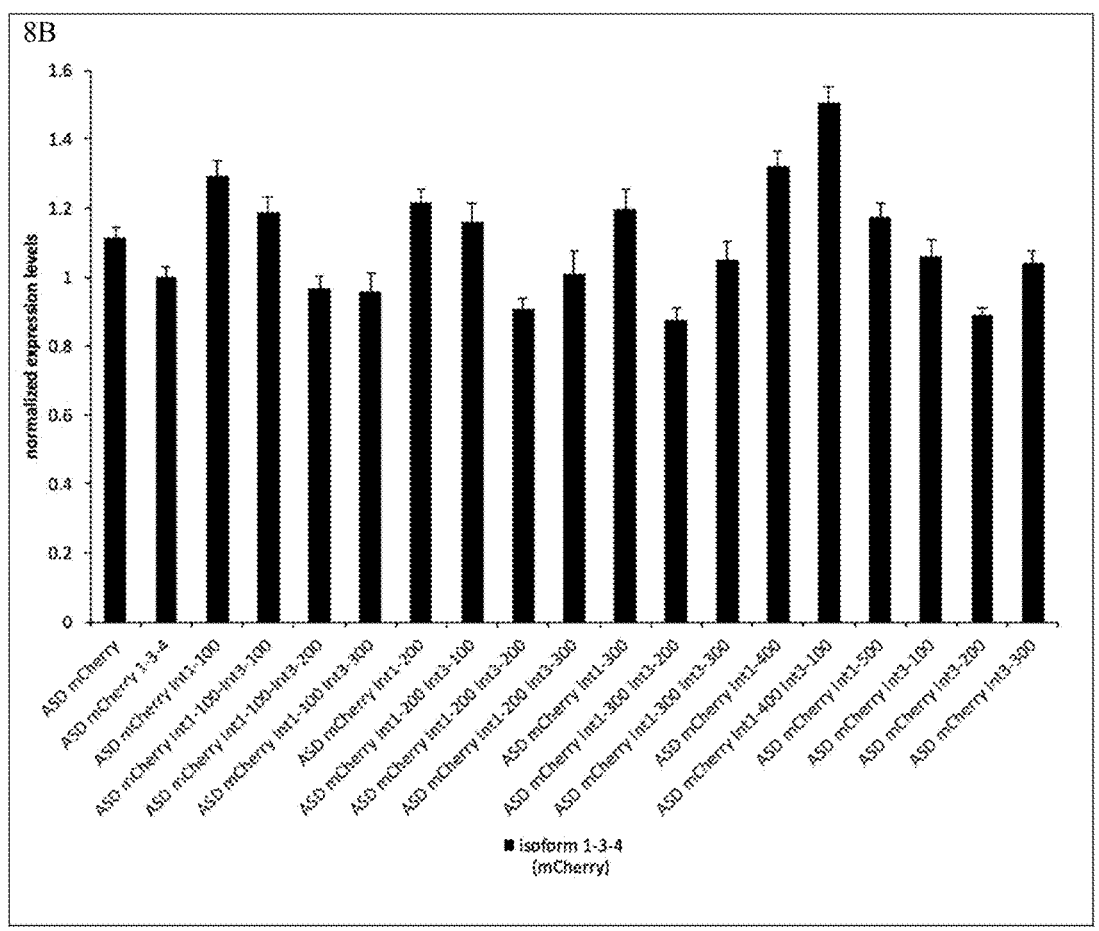

The intron sequences surrounding the exons can be lengthened to introduce regulatory sequences or truncated to remove regulatory elements or decrease the size of the device. Intron sizes for each intron can range from 100-1000 nucleotides, but are not limited to this range (FIG. 8).

In certain embodiments, targeted changes can be made to the exon sequences within the alternative splicing device to mutate or remove cryptic splice site elements that prevent proper recognition of the defined exon-intron junctions within the alternative splicing device.

Applications in Controlling Gene Expression

Alternative splicing devices that program modular transcription factors for gene control are described below.

Modular transcription factors are composed of interchangeable modules that can be constructed in a reliable manner by combining DNA binding domains and effector domains to stimulate or inhibit the expression of a target gene (Zhang et al Nat. Biotechnol. 2011 29: 149-53; Garg et al, Nucleic Acids Res 2012 40: 7584-95). The ability to regulate the expression of any target gene by reprogramming a modular transcription factor makes it a powerful tool for transcription-based therapeutics. Prior research in this area has focus on constructing and thoroughly characterizing a variety of modules or domains within modular transcription factors and then programming them prior to their introduction to the cell for gene control.

This alternative splicing device platform enables programming modular transcription factors in vivo in response to factors (i.e., proteins, small molecules, and/or DNA and RNA oligonucleotides) added to or present within the cellular environment. In this way, the cellular response can be tuned by altering the DNA binding domain or effector domains. This type of in vivo reprogramming will allow for improved control and expand the ability of devices to integrate within cellular networks to interact with or alter cellular programs.

This alternative splicing device is an RNA molecule with an input module composed of a control element integrated near a regulatory sequence element and an output module composed of mutually exclusive protein coding sequences, or exons, which encode variable internal protein sequence that encode portions of domains of a modular transcription factor (i.e., DNA binding domains, effector domains, etc.) and are nested within external coding sequences, that can undergo alternative splicing. Upon activation of the control element in the input module, the state of the regulatory sequence element is altered to change the alternative splicing pattern and select a mutually exclusive exon that differs from default to change the modular transcription factor generated by the device.

The input module functions to detect the cellular environment and modulate the accessibility of an essential regulatory element. The control element can be a small molecule aptamer, protein aptamer, and/or DNA or RNA oligonucleotide binding site. The small molecule, protein, or DNA/RNA oligonucleotide can be added exogenously to the cell or generated endogenously within the cell.

The output module is comprised of a set of exons with interspaced intronic sequences capable of undergoing mutually exclusive splicing. In an example, an output module comprised of a first exon, a first intron, a second exon, a second intron, a third exon, and third intron, and a fourth exon that encode different segments of a modular transcription factor. Domains in a modular transcription factor can be split into artificial exons, such that the insulator sequences can be integrated and required exons sizes maintained.

Figure 9:
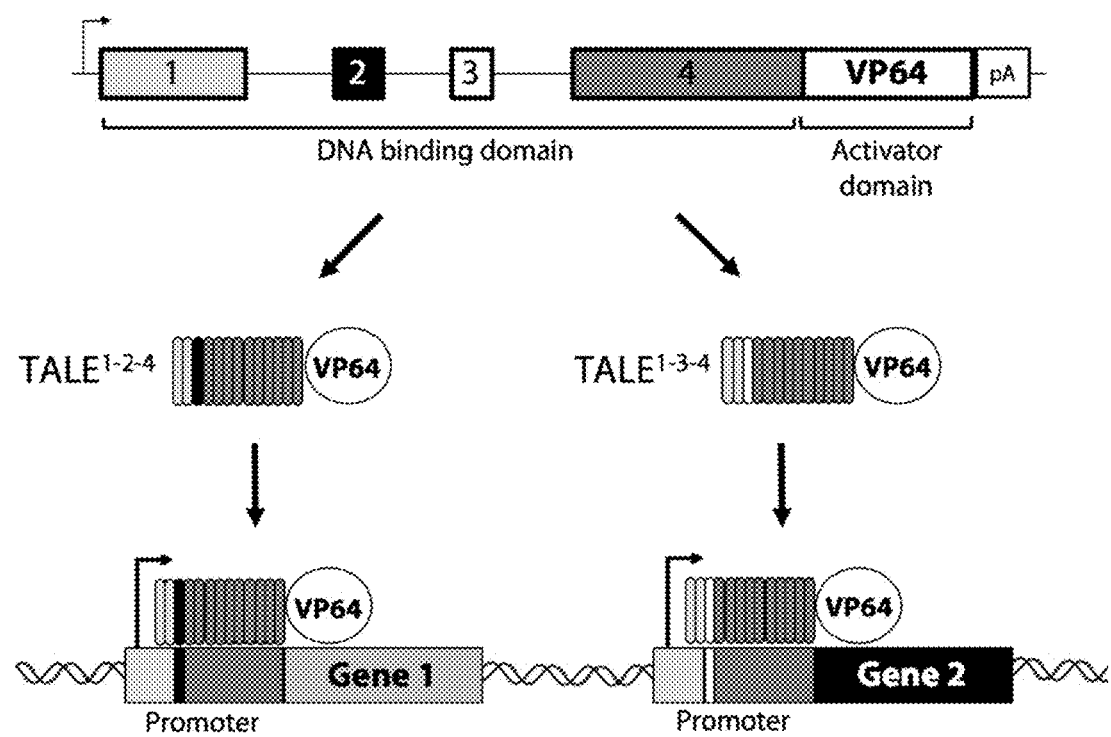
FIG. 9 shows an alternative splicing device for programming modular transcription factors.

In one embodiment, the DNA binding domains are split into artificial exons and these exons are incorporated into the four exon-three intron mutually exclusive splicing device. To modulate the expression of two modular transcription factors, domains can be segmented such that variable segments of a DNA binding domain are encoded within the mutually exclusive exons. These exons are then incorporated into the intron framework such that the DNA binding domain is encoded within exons 1-4 and the effector domain is encoded within exon 4 or appended to the end of the device (FIG. 9).

In certain embodiments, the alternative splicing device programs a specific class of modular transcription factors called transcription activator-like effector (TALE) transcription factors. The DNA binding domain is programmed by the combination of exons 1-2-4 or exons 1-3-4. With exons 2 and 3 being variable in this device, the segment of the DNA binding domain that is encoded in this sequence alters the DNA binding domain in response to the splicing event. The activation domain, such as VP64, or alternatively VP16 or any natural, synthetic, or evolved effector domain, can be included within exon 4 or appended to the end of the alternative splicing device. In this manner, a DNA binding domain can be constructed to bind any target gene within the genome.

In one embodiment, the transcription factor can be programmed to bind the DNA sequence "TACGACTCACTATA" (SEQ ID NO: 1) or the DNA sequence Jo "TACTACTCACTATA" (SEQ ID NO:2). The residues that bind the variable nucleotides in the target DNA sequence are encoded in the mutually exclusive exons, while the initial section of the DNA binding domain that is consistent in both domains is encoded by exon 1 and the latter section is within exon 4. Therefore, exon 1 contains the shared segment of the DNA binding domain, exon 2 contains residues that bind "T", while exon 3 contains residues that bind "G", and exon 4 encodes the remaining segment of the DNA binding domain and the activation domain, such as VP64, within the intron framework. This alternative splicing device splices to produce the dominant transcription factor that binds sequence "TACGACTCACTATA" (SEQ ID NO: 1) and the alternate transcription factor binds sequence "TACTACTCACTATA" (SEQ ID NO:2) (FIG. 10A).

In another embodiment, the incorporation strategy can also be reversed such that the variable segment of the DNA binding domain that binds "T" is encoded by exon 3 and the segment that encodes that portion that binds "G" is encoded by exon 2. This alternative splicing device splices to produce the dominant transcription factor that binds sequence "TACTACTCACTATA" (SEQ ID NO:2) and the alternate transcription factor binds sequence "TACGACTCACTATA" (SEQ ID NO:1) (FIG. 10A).

In another embodiment, DNA binding domains that recognize alternate binding sites can be incorporated into the exons. The transcription factor can be programmed to bind the DNA sequence "TTTTGTTTTCTTTA" (SEQ ID NO:3) or the DNA sequence "TTTGTCCTCTTTA" (SEQ ID NO:4). The residues that bind the variable nucleotides in the target DNA sequence are encoded in the mutually exclusive exons, while the initial section of the DNA binding domain that is consistent in both domains is encoded by exon 1 and the latter section is within exon 4. Therefore, exon 1 contains the shared segment of the DNA binding domain, exon 2 contains residues that bind "CC", while exon 3 contains residues that bind "TT", and exon 4 encodes the remaining segment of the DNA binding domain and the activation domain, such as VP64, within the intron framework. This alternative splicing device splices to produce the dominant transcription factor that binds sequence "TTTTGTTTTCTTTA" (SEQ ID NO:3) and the alternate transcription factor binds sequence "TTTTGTCCTCTTTA" (SEQ ID NO:4) (FIG. 10B).

In another embodiment, the incorporation strategy can also be reversed such that the variable segment of the DNA binding domain that binds "CC" is encoded by exon 3 and the segment that encodes that portion that binds "TT" is encoded by exon 2. This alternative splicing device splices to produce the dominant transcription factor that binds sequence "TTTTGTCCTCTTTA" (SEQ ID NO:4) and the alternate transcription factor binds sequence "TTTTGTTTTCTTTA" (SEQ ID NO:3) (FIG. 10B).

In certain embodiments, additional mutually exclusive exons and introns can be added into the alternative splicing device to increase the number of exons available for selection and increase the number of fluorescent reporters encoded by the device. In these embodiments, exons 1 and 4 encode constant regions of the DNA binding domains and the mutually exclusive exons encode segments that alter precise residues to change the target sequence the transcription factor binds.

In certain embodiments, regulatory sequence elements can be tuned to alter the behavior of the alternative splicing device. Such changes can effect the incompatibility of mutually exclusive exons, change the default state of the device, eliminate the requirement of another regulatory sequence element, or strengthen the role of a particular regulatory sequence element. Regulatory sequence elements, including but not limited to 5' splice sites, 3' splice sites, branch point sequences, polypyrimidine tracts, intronic splicing enhancers, intronic splicing silencers, exonic splicing enhancers, and exonic splicing silencers, can be truncated, added, mutated, replaced, or incorporated in novel combinations to weaken, strengthen, or alter the device's performance.

The length of the mutually exclusive exons is variable and can vary from 50-250 nucleotides, but is not limited to this range. The first and last exons in the device have no limitations on length.

The intron sequences surrounding the exons can be lengthened to introduce regulatory sequences or truncated to remove regulatory elements or decrease the size of the device. Intron sizes for each intron can range from 100-1000 nucleotides, but are not limited to this range.

In certain embodiments, targeted changes can be made to the exon sequences within the alternative splicing device to mutate or remove cryptic splice site elements that prevent proper recognition of the defined exon-intron junctions within the alternative splicing device.

EXAMPLES

Aspects of the present teachings can be further understood in light of the following example, which should not be construed as limiting the scope of the present teachings in any way.

Alternative Splicing Device Constructs

Plasmids were constructed using standard molecular biology techniques and Gibson assembly. DNA synthesis was performed by Integrated DNA Technologies, Inc and Stanford Protein and Nucleic Acid Facility. All enzymes, including restriction enzymes and ligases, were obtained through New England Biolabs unless otherwise noted. The alternative splicing devices (ASD GFP, ASD mCherry, modular transcription factor splicing devices and all the regulatory sequence element modifications and associated controls) were constructed through a PCR assembly, Gibson assembly, or site-directed mutagenesis strategy. The resulting alternative splicing devices and associated controls were cloned into the mammalian expression vector pcDNA5/FRT (Life Technologies). Gibson assembly products and ligation products were transformed into chemically-competent *Escherichia coli* strain TOP10 by heat shock and clones were verified through colony polymerase chain reaction (PCR). All cloned constructs were sequence verified by Elim Biopharmaceuticals, Inc.

Mammalian Cell Culture and Flow Cytometry

HEK293 Flp-In cells (Life Technologies) were maintained in DMEM supplemented with 10% FBS at 37° C. in a 5% CO2-humidified incubator. Cell lines were transiently transfected with the alternative splicing device plasmids. Experiments were performed by seeding 24-well cell culture plates at $5.0 \times 10^4$ cells per well. Cells were transfected after 24 hours with 500 ng plasmid using the Lipofectamine 2000 reagent (Life Technologies). 48 hours after transfection, cells were trypsinized and subjected to flow cytometry analysis on the MAQSQuant VYB (Miltenyi Biotec) and the resulting data were analyzed using the FlowJo software. At least two biological replicates were included in each experiment. Error bars represent ±1 standard deviation.

Pacific Biosciences RNA Sequencing and Data Analysis

Library preparation was performed using standard Pacific Biosciences sequencing procedure. Reverse transcription of the spliced isoforms for each alternative splicing device was performed separately and the cDNAs were amplified by PCR. SMRT bell sequencing libraries were prepared using Pacific Biosciences DNA Template Prep Kit 2.0 according to the 2-kb template preparation and sequencing protocol. SMRT bell templates were bound to polymerases using DNA Polymerase Binding Kit (P4 polymerase). Sequencing was carried out on the Pacific Biosciences RSII using C2 sequencing reagents. Subread filtering was performed using Pacific Biosciences SMRT analysis software.

Example 1

Figure 1:
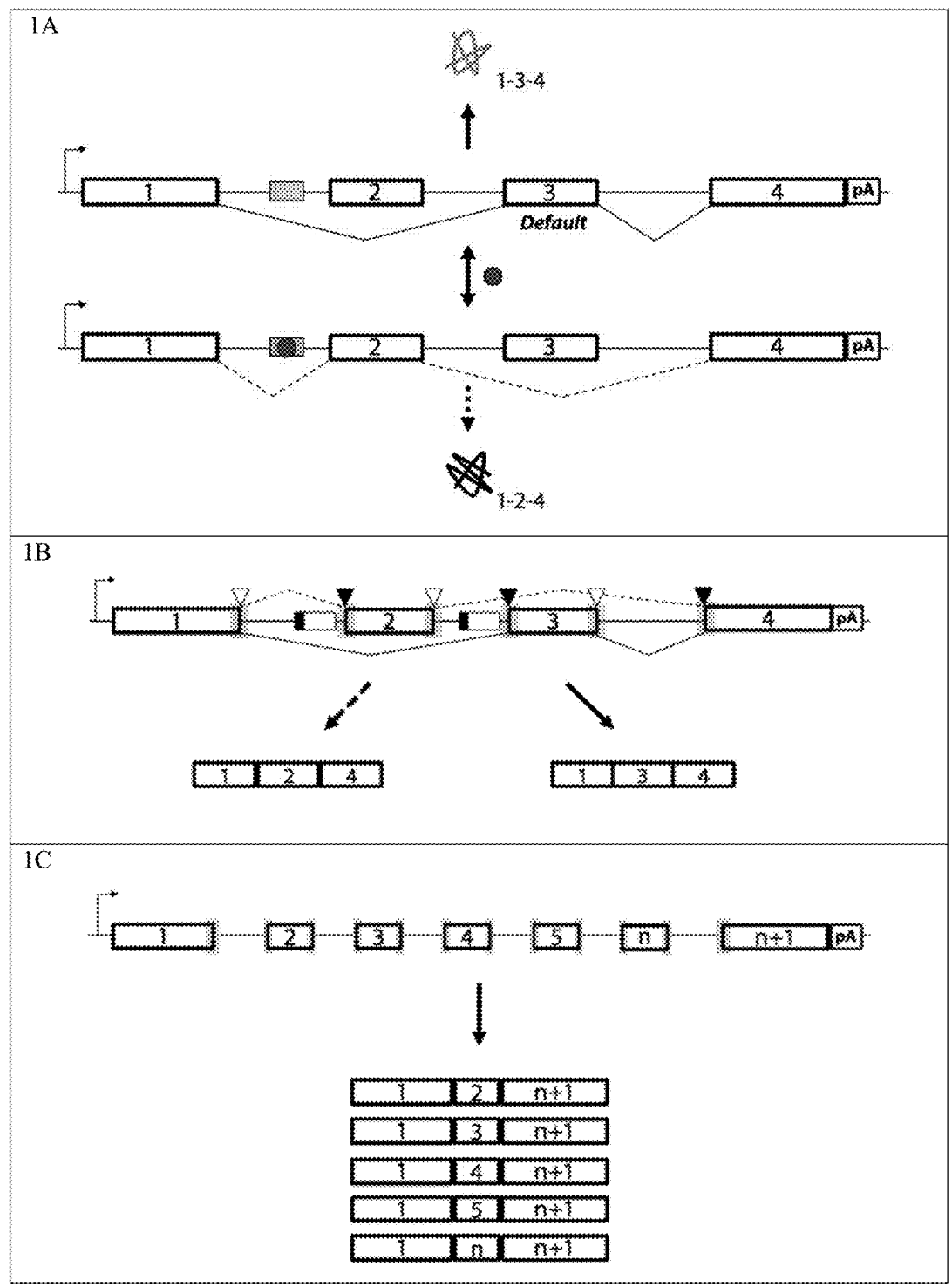
FIG. 1 schematically illustrates a modular and extensible alternative splicing device intron framework supports mutually exclusive alternative splicing.

A Modular and Extensible Alternative Splicing Device Intron Framework Supports Mutually Exclusive Alternative Splicing FIG. 1 illustrates an alternative splicing intron framework that supports alternative splicing events. (A) An input module consists of a control element (gray box) that is integrated near a regulatory sequence element. The output module is composed of a set of exons that can undergo alternative splicing. In this is example, a four exon-three intron design can produce two mutually exclusive products, protein isoform 1-3-4 and protein isoform 1-2-4. The default selection is exon 3. Upon detection of an input (black circle) by the control element, the alternative splicing pattern switches to select the protein isoform 1-2-4. (B) A number of regulatory sequences are present within the alternative splicing device, including the 5' splice sites (white inverted triangle), 3' splice sites (black inverted triangle), branch point sequences (black rectangles), and polypyrimidine tracts (white rectangles). Sequence elements such as exonic splicing enhancers, exonic splicing silencers, intronic splicing enhancers, and intronic splicing silencers can also be present or incorporated into the device (not pictured). Insulator sequence elements (gray boxes) are integrated at the exon-intron junction to maintain the identity of the junctions, promote proper exon recognition, and limit crosstalk between the input module and the output module. (C) Additional mutually exclusive exons can be incorporated to increase the number of protein isoforms encoded by the alternative splicing device.

Example 2

Sequence Elements Enforce Mutually Exclusive Splicing Events in Alternative Splicing Device FIG. 2 shows sequence elements that are introduced into the intron framework of the alternative splicing device to enforce mutually exclusive splicing events. As an example, a distance shorter than 50 nucleotides between the second exon's 5' splice site (white inverted triangle) and the third exon's branch point sequence (black rectangle), as indicated by the oval, inhibits proper spliceosomal assembly and renders the middle two exons incompatible. In this situation, the physical constraint prevents double inclusion of the mutually exclusive exons and the output module splices to only include one mutually exclusive exon.

The aptamer in intron 1, which can be integrated within any intron, binds to a small molecule input. Small molecule binding drives switching between the two structural states, one fold will leave the regulatory sequence element accessible while it is hidden in the other. A linker sequence (black rectangle) between the aptamer and regulatory sequence element (gray box), allows for switching between two structural folds.

Example 3

Figure 3:
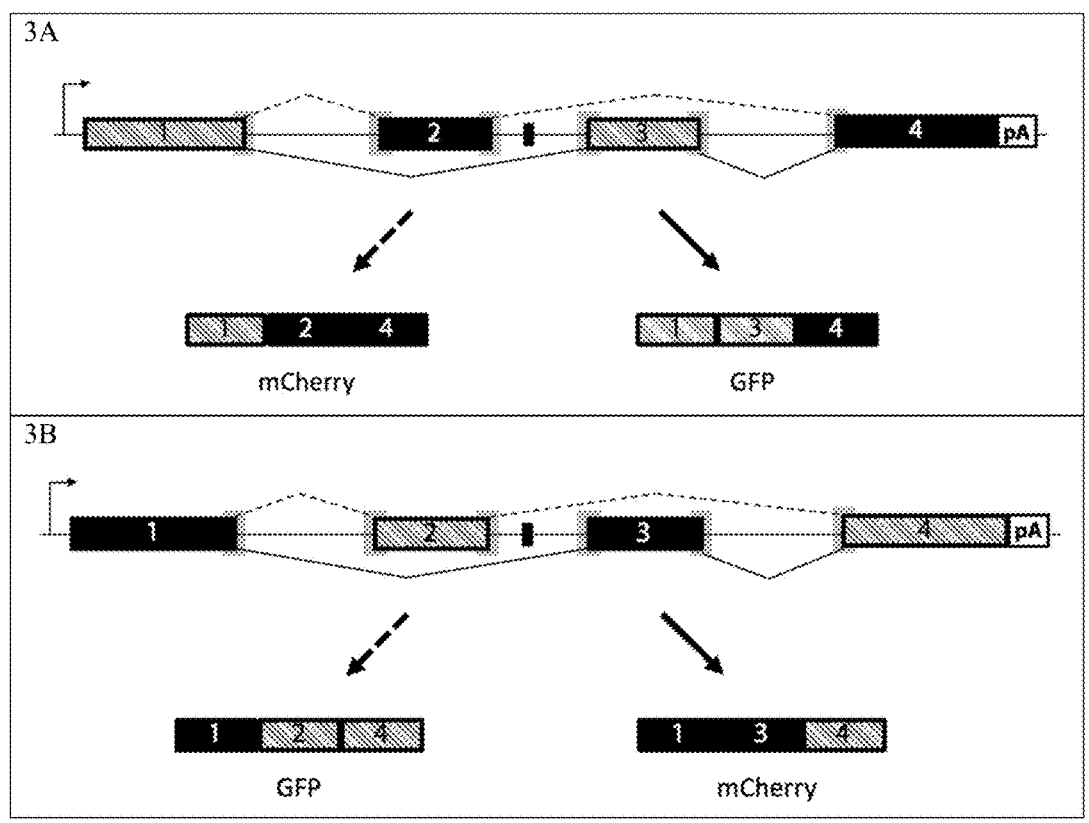
FIG. 3 schematically illustrates two embodiments of alternative splicing devices that program fluorescent proteins.

Two Embodiments of Alternative Splicing Devices that Program Fluorescent Proteins FIG. 3 shows two distinct alternative splicing devices can be used to program fluorescent protein expression. (A) In the first embodiment, the fluorescent proteins are split into artificial exons and incorporated into the intron framework such that the dominant isoform (through a splicing event denoted by the solid lines) is protein isoform 1-3-4 or GFP. The alternate mutually exclusive splicing product (through a splicing event indicated by dashed lines) produces protein isoform 1-2-4 or mCherry. (B) In a second embodiment, the default isoform (through a splicing event denoted by the solid lines) produced by protein isoform 1-3-4 is mCherry and the alternate form (through a splicing event indicated by dashed lines) is isoform 1-2-4, or GFP.

Example 4

Two Alternative Splicing Devices that Splice to Produce the Default Isoform

Figure 4:
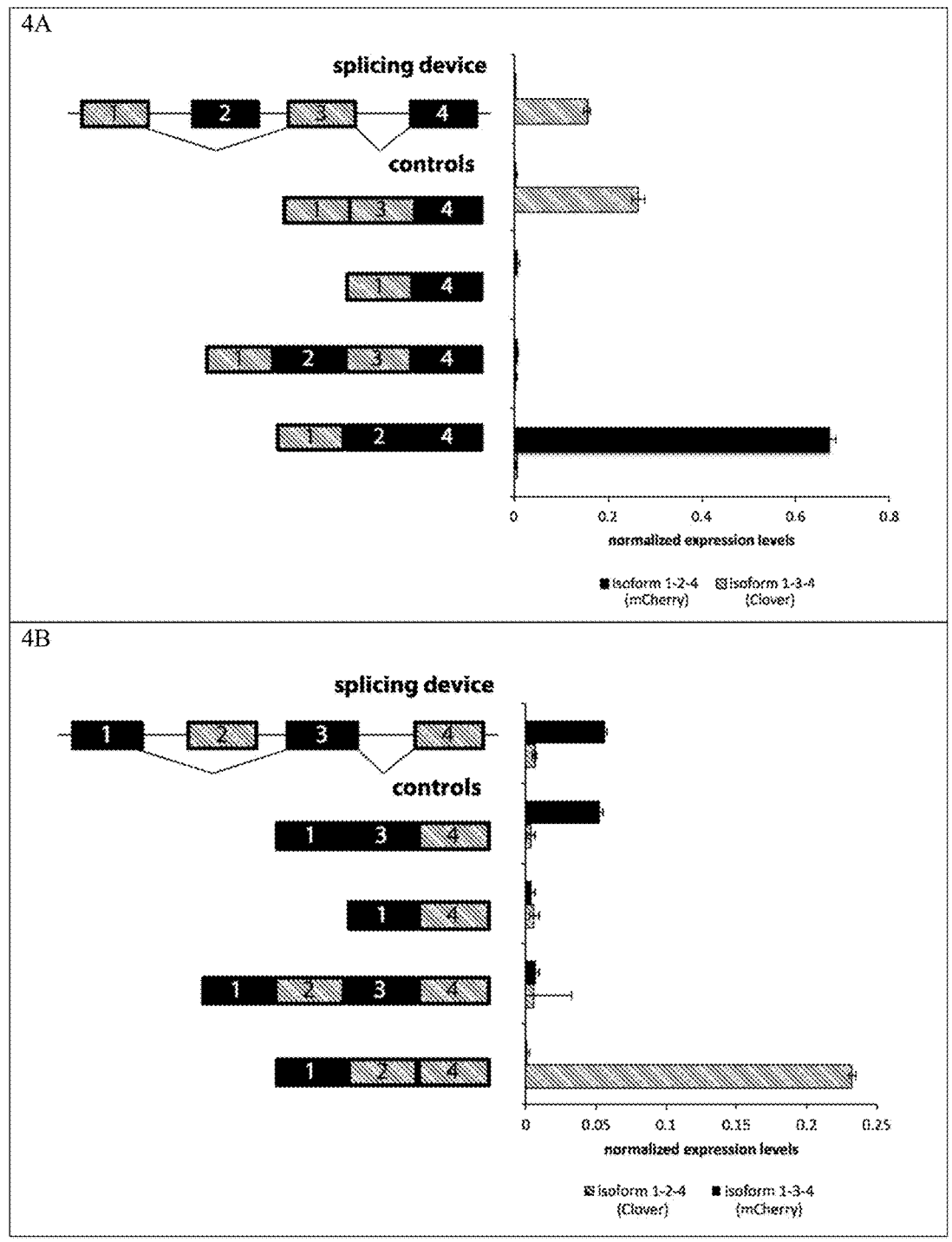
FIG. 4 schematically illustrates two alternative splicing devices that splice to produce the default isoform.

FIG. 4 shows the alternative splicing devices are validated by transfection of these devices into mammalian cells followed by subsequent flow cytometry and analysis. Pre-spliced devices serve as controls for fluorescent protein expression levels. (A) The alternative splicing device that splices to the default state of isoform 1-3-4 produces GFP (ASD GFP). (B) A different alternative splicing device that is designed to express mCherry as the default isoform expresses mCherry at levels comparable to the pre-spliced control with isoform 1-3-4 (ASD mCherry).

Example 5

The Effect of Various Regulatory Sequence Elements in Alternative Splicing Device (ASD) GFP FIG. 5 shows that regulatory sequence elements can tune the behavior of the alternative splicing device that produces the default isoform 1-3-4 of GFP. (A) Mutating the branch point sequence or polypyrimidine tract sequence elements upstream of the mutually exclusive exons alters splicing patterns. Mutating exon 3's branch point sequence weakens 1-3-4 isoform production while increasing 1-2-4 isoform levels. Mutating exon 2's branch point sequence seems to have a minimal effect. Meanwhile, mutating exon 2's polypyrimidine tract or both the branch point and polypyrimidine tract increases 1-2-4 isoform levels while greatly decreasing 1-3-4 isoform levels. (B) The polypyrimidine tract upstream of exon 3 can be truncated to shut down the expression of both isoforms. (C) The branchpoint sequence, 3' splice site, and 5' splice site of exon 3 can be mutated to alter the behavior of the device. Mutating the branch point sequence greatly decreases 1-3-4 isoform levels, coupled to the appearance of the 1-2-4 isoform. The 3' splice site mutation has a minimal effect on 1-3-4 isoform levels, while the 5' splice site mutation increases GFP levels. (D) Combining a number of individual modifications allows for switching between the expression of two distinct isoforms. Modifying exon 2's branch point and polypyrimidine tract sequences and exon 3's branch point sequences allows for the robust expression of isoform 1-3-4 with certain combinations of regulatory elements and the expression of isoform 1-2-4 with other elements.

Example 6

Figure 6:
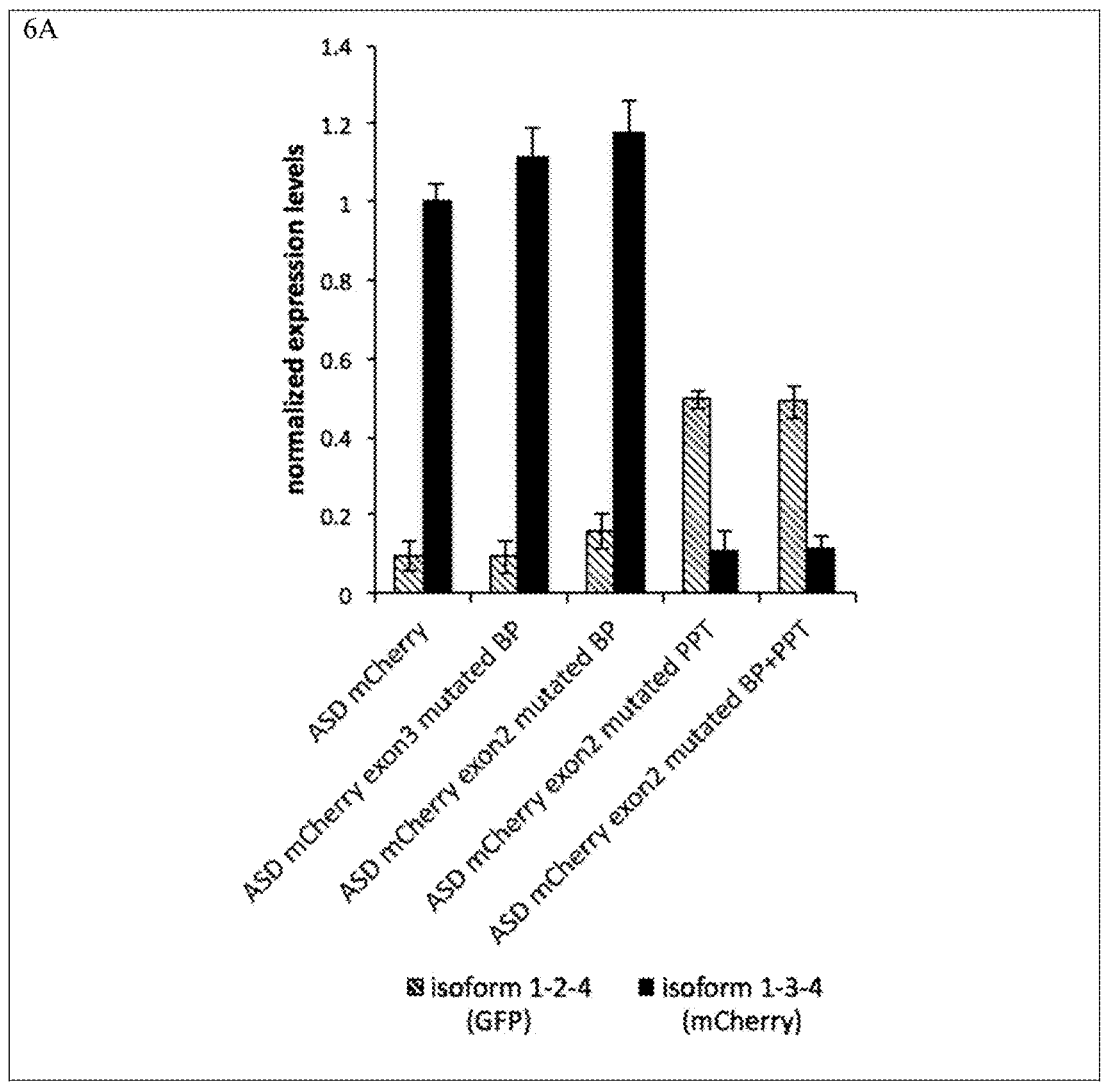
FIG. 6 shows the effect of various regulatory sequence elements in alternative splicing device (ASD) mCherry.
Figure 6:
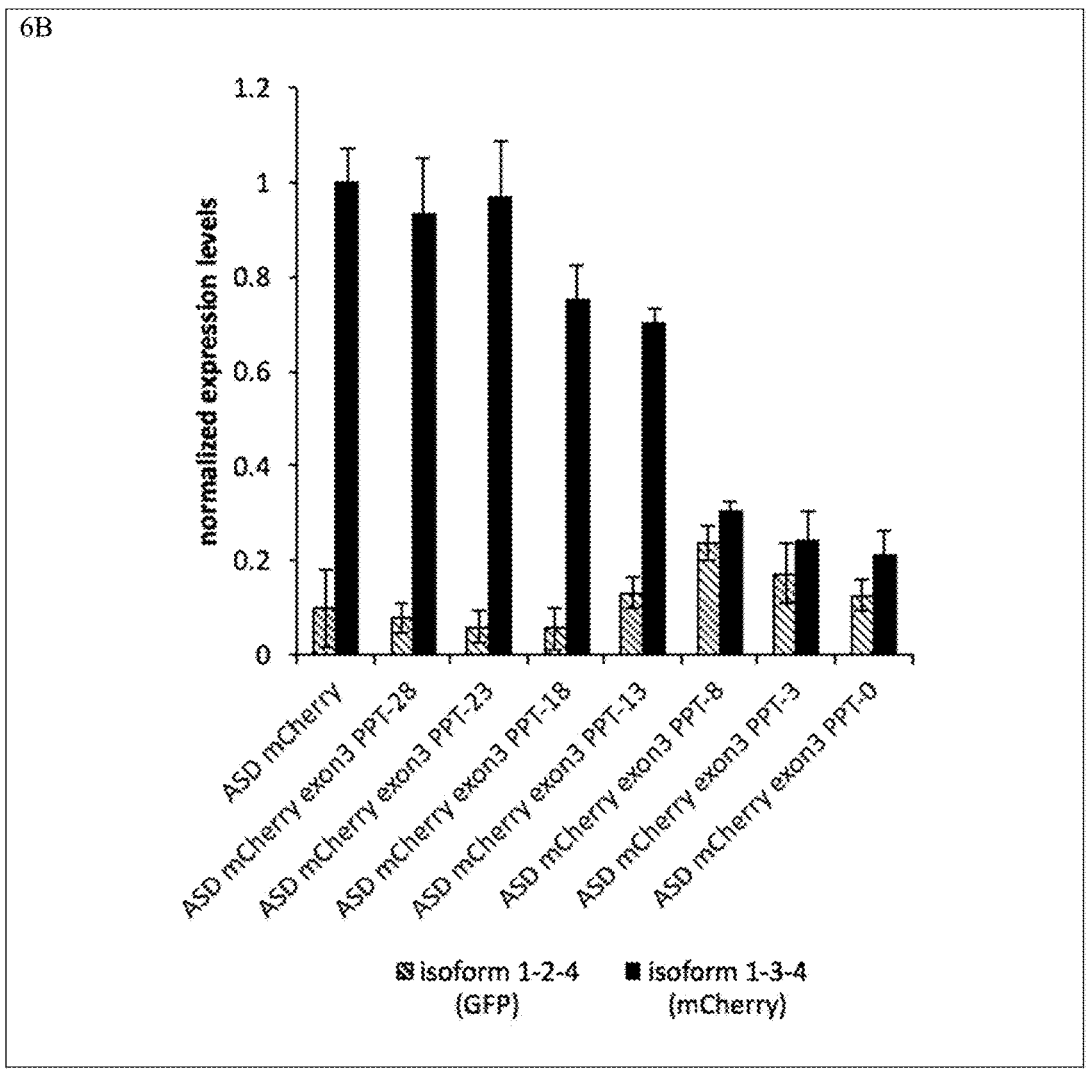
Figure 6:
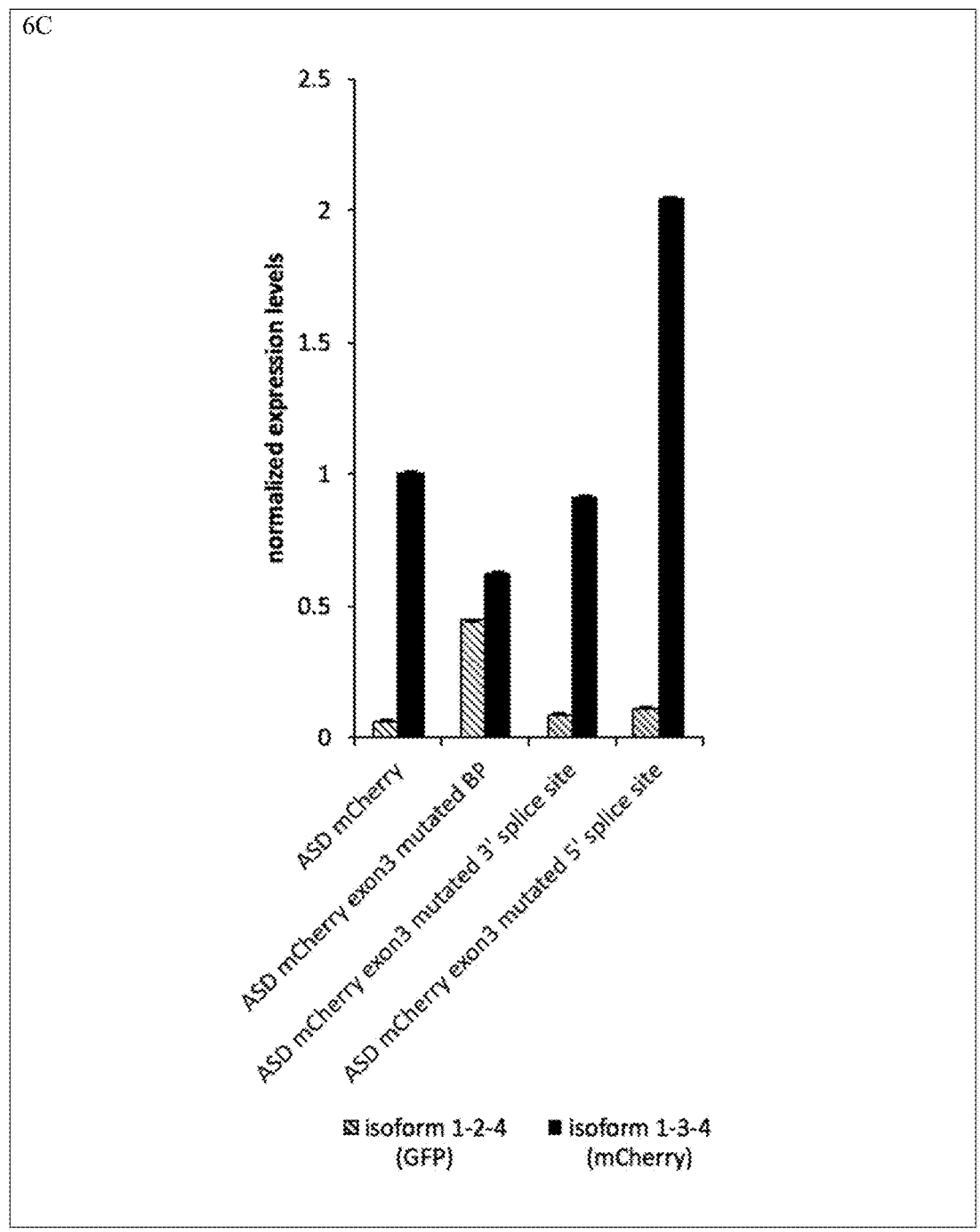
Figure 6:
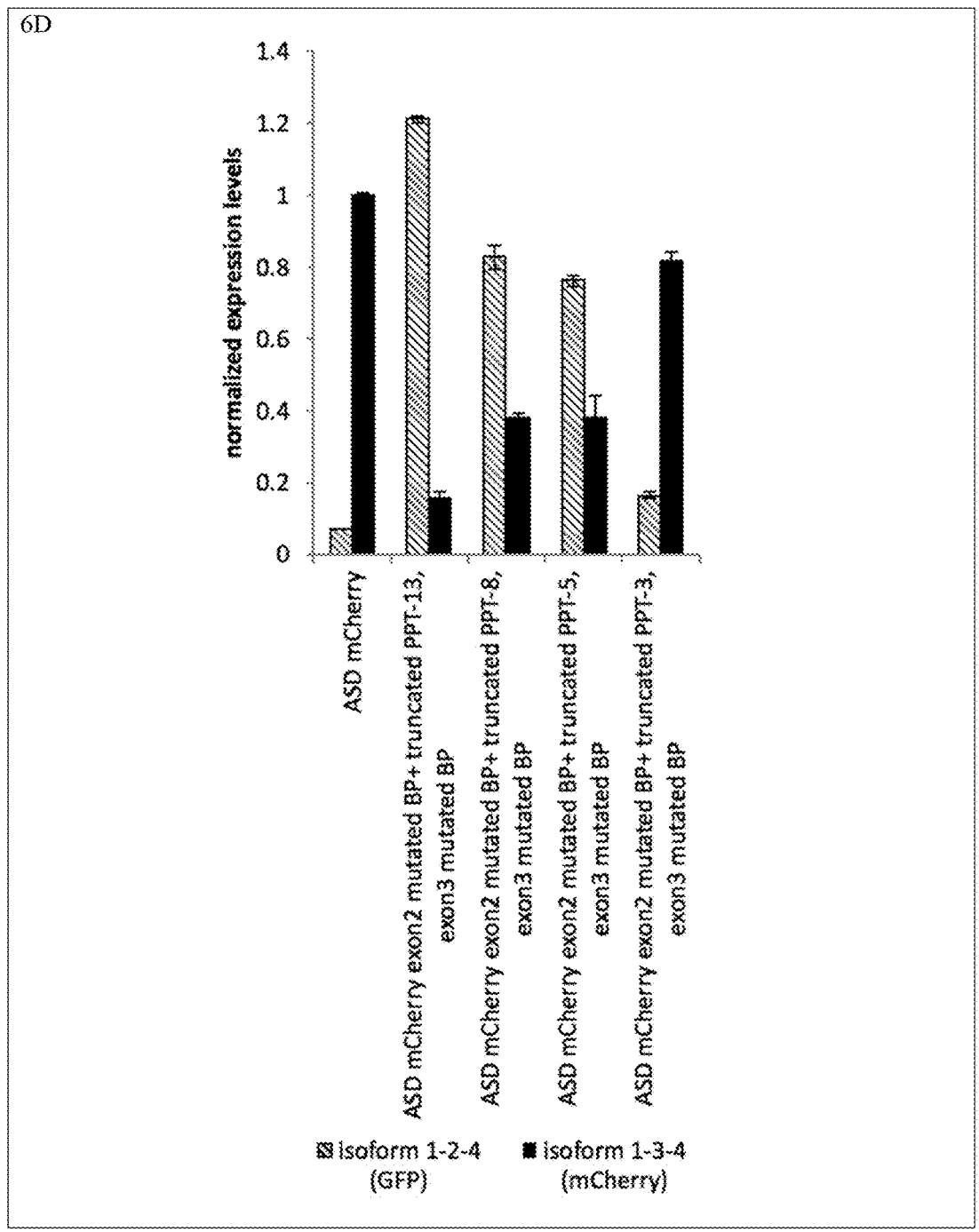

The Effect of Various Regulatory Sequence Elements in Alternative Splicing Device (ASD) mCherry FIG. 6 shows regulatory sequence elements can tune the behavior of the alternative splicing device that produces the default isoform 1-3-4 of mCherry. (A) Mutating the branch point sequence or polypyrimidine tract sequence elements upstream of the mutually exclusive exons alters splicing patterns. Mutating exon 3's branch point sequence or exon 2's branch point sequence seems to have a minimal effect. Meanwhile, mutating exon 2's polypyrimidine tract or both the branch point and polypyrimidine tract increases 1-2-4 isoform levels while greatly decreasing 1-3-4 isoform levels. (B) The polypyrimidine tract upstream of exon 3 can be truncated to shut down the expression of both isoforms. (C) The branchpoint sequence, 3' splice site, and 5' splice site of exon 3 can be mutated to alter the behavior of the device. Mutating the branch point sequence greatly decreases 1-3-4 isoform levels, coupled to the appearance of the 1-2-4 isoform. The 3' splice site mutation has a minimal effect on 1-3-4 isoform levels, while the 5' splice site mutation increases mCherry levels. (D) Combining a number of individual modifications allows for switching between the expression of two distinct isoforms. Modifying exon 2's branch point and polypyrimidine tract sequences and exon 3's branch point sequences allows for the robust expression of isoform 1-3-4 with certain combinations of regulatory elements and the expression of isoform 1-2-4 with other elements.

Example 7

Varying Exon Sizes within the Two Embodiments of Alternative Splicing Devices that Express Fluorescent Proteins FIG. 7 shows the mutually exclusive exons within that alternative splicing device can range from 50-250 nucleotides. (A) In the ASD that produces GFP as the default isoform, exon 2 is 111 nucleotides and exon 3 is 117 nucleotides. In the ASD with longer mutually exclusive exons (MXE), exon 2 is 129 nucleotides and exon 3 is 135 nucleotides. (B) In the ASD that produces mCherry as the default isoform, exon 2 is 126 nucleotides and exon 3 is 132 nucleotides. In the ASD with longer mutually exclusive exons (MXE), exon 2 is 144 nucleotides and exon 3 is 150 nucleotides.

Example 8

Varying Intron Sizes within the Two Embodiments of Alternative Splicing Devices that Express Fluorescent Proteins FIG. 8 shows intron sizes within the device can range from 100-1000 nucleotides. (A) In ASD GFP, intron 1 is approximately 800 nucleotides long and can be truncated down to approximately 200 nucleotides. Intron 3 is approximately 500 nucleotides and can be truncated down to 100 nucleotides. The intron 1 and intron 3 truncations can be combined to further shorten the sequence and make a smaller device. (B) In ASD mCherry, intron 1 is approximately 800 nucleotides long and can be truncated down to approximately 200 nucleotides. Intron 3 is approximately 500 nucleotides and can be truncated down to 100 nucleotides. The intron 1 and intron 3 truncations can be combined to further shorten the sequence and make a smaller device.

Example 9

Alternative Splicing Device for Programming Modular Transcription Factors

FIG. 9 shows modular transcription factors can be incorporated into the alternative splicing device. In one embodiment, the alternative splicing device encodes the DNA binding domain of a modular transcription factor. Segments of the DNA binding domain that allow the transcription factor to recognize distinct binding sites are encoded by the mutually exclusive exons. The activator domain, VP64, is appended to the alternative splicing device. By altering the DNA binding domain, the alternative splicing device can dynamically program gene control.

Example 10

Programming Modular Transcription Factors with the Alternative Splicing Device

Figure 10:
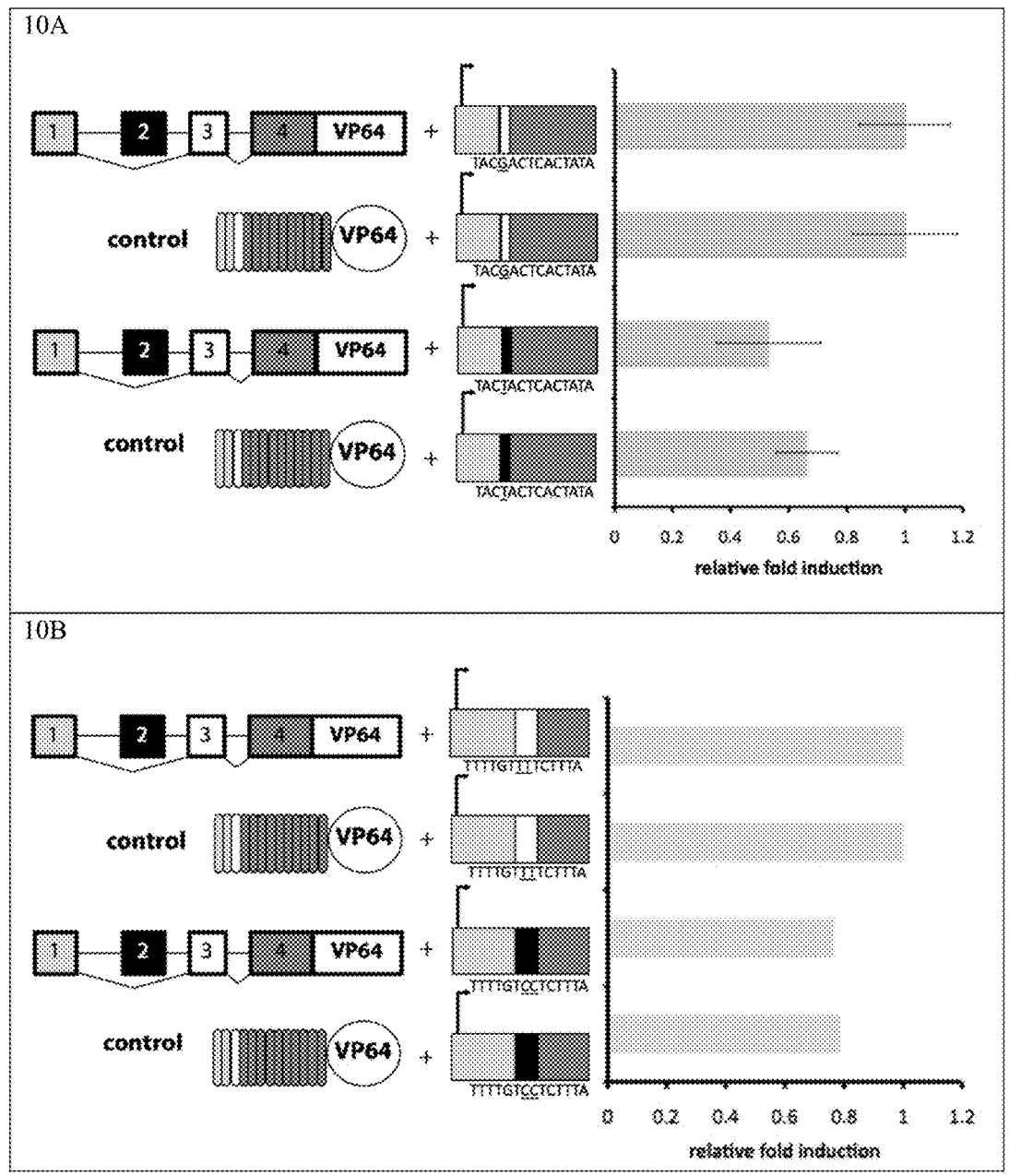
FIG. 10 shows a way for programming modular transcription factors with the alternative splicing device (SEQ ID NOs: 1-4).

FIG. 10 shows the DNA binding domain of the modular transcription factor is so incorporated into the alternative splicing device. (A) In the first pair at the top of the figure, the DNA binding domain is programmed to bind "TAC GACTCACTATA" (SEQ ID NO: 1) when exon 3 is selected to produce the transcription factor. Both the transcription factors with the spliced DNA binding domain and pre-spliced DNA binding domain bind the target site and induce gene expression at similar levels. In the second pair, the same alternative splicing device is added to a cell containing a target site with one nucleotide difference, "TAC TACTCACTATA." (SEQ ID NO:2). Again, both the transcription factors with the spliced DNA binding domain and pre-spliced DNA binding domain bind the target site and induce gene expression at similar levels. (B) In the first pair, the DNA binding domain is programmed to bind "TTTTGT TTTCTTTA" (SEQ ID NO:3) when exon 3 is selected to produce the transcription factor sequence. Both the transcription factors with the spliced DNA binding domain and pre-spliced DNA binding domain bind the target site and induce gene expression at similar levels. In the second pair, the same alternative splicing device is added to a cell containing a target site with a two nucleotide difference. "TTTTGTCCTCTTTA." (SEQ ID NO:4). Again, both the transcription factors with the spliced DNA binding domain and pre-spliced DNA binding domain bind the target site and induce gene expression at similar levels.

Example 11

The Effect on Splicing Outcome from Targeted Modifications to Alternative Splicing Regulatory Sequence Elements FIG. 11 shows a number of regulatory sequence elements can be truncated, added, mutated, replaced, or incorporated in novel combinations to weaken, strengthen, or alter the device's performance. Targeted modifications at specific sites are indicated by symbols: 5' splice sites (white inverted triangle), 3' splice sites (black inverted triangle), branch point sequences (black rectangles), and polypyrimidine tracts (white rectangles). The expected isoform products and isoform levels, normalized to pre-spliced 1-2-4 and 1-3-4 constructs that serve as controls across experiments and are noted as percentages, indicate the isoform profile after the splicing event. Modifications that increase expression levels are noted by a percentage that exceeds 100%. Modifications made in combination can have varying effects on the percentage of each isoform produced depending on which sequence elements are incorporated into the device.

It will also be recognized by those skilled in the art that, while the invention has been described above in terms of embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

Example 12

Figure 12:
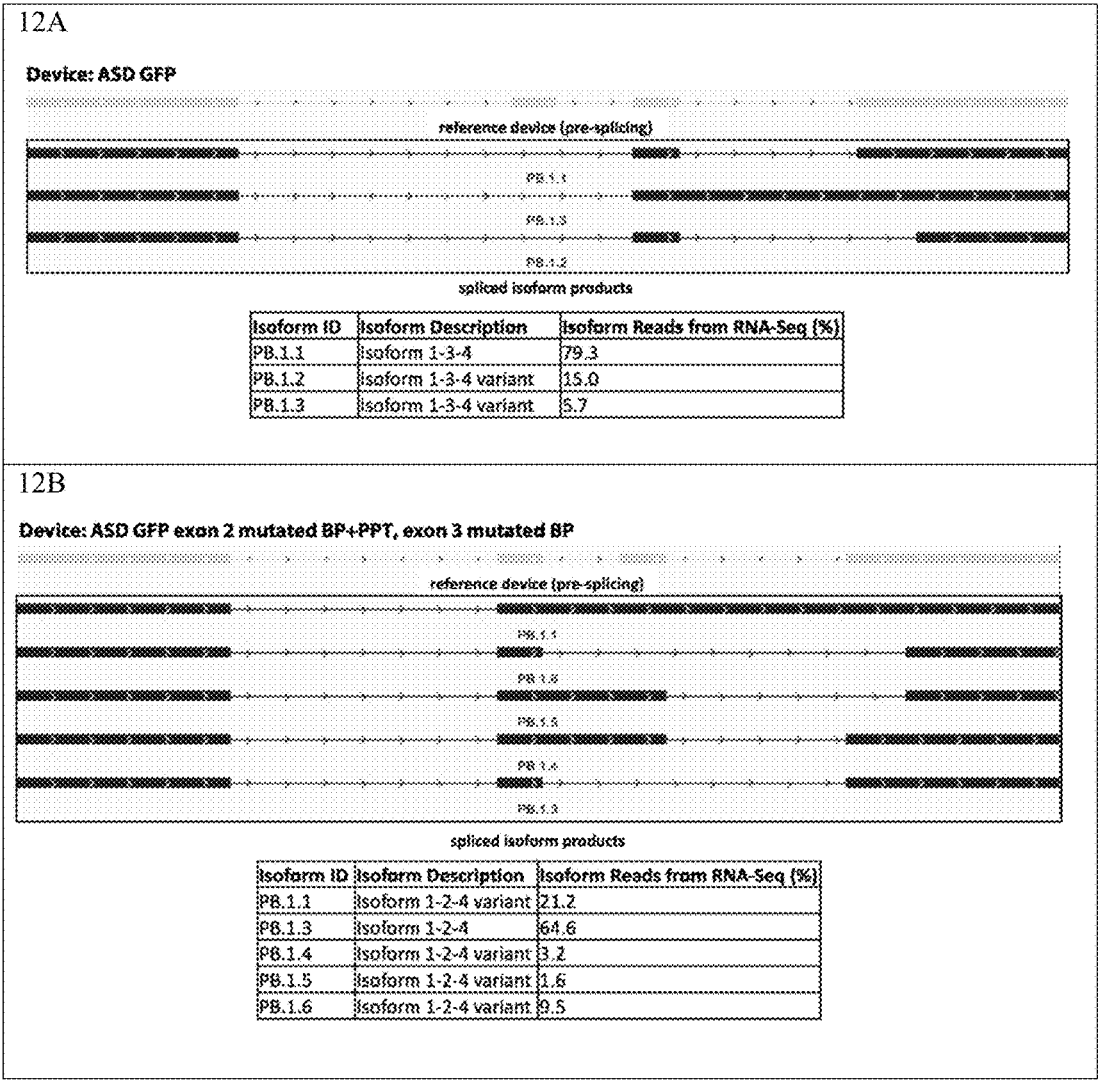
FIG. 12 shows the signature of alternative splicing devices derived from the two alternative splicing devices (ASD) GFP and mCherry
Figure 12:
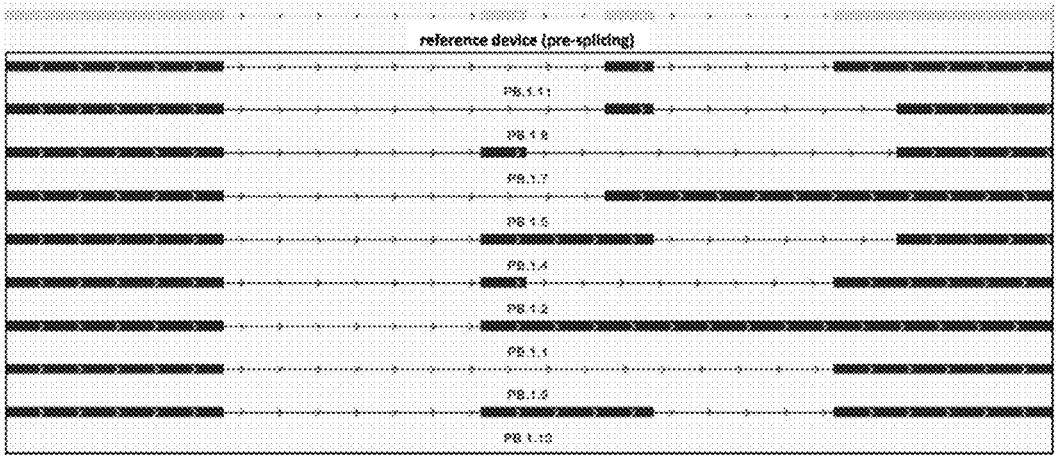
Figure 12:
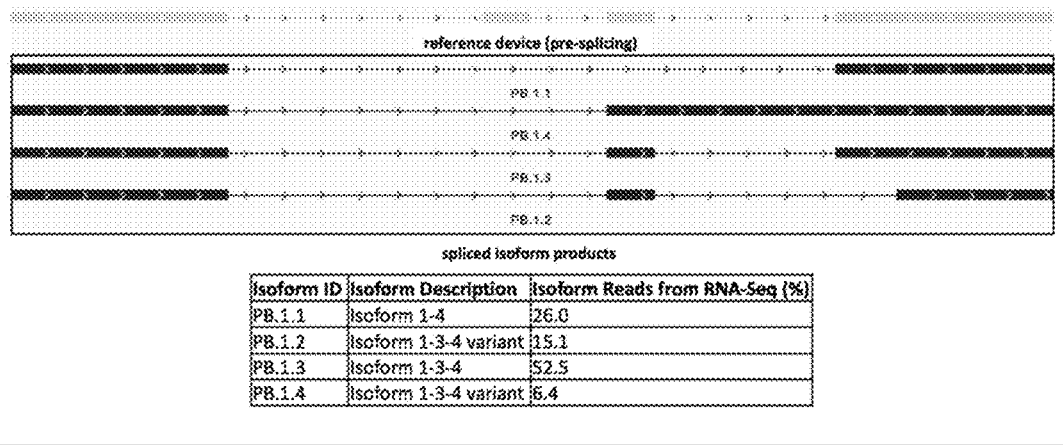
Figure 12:
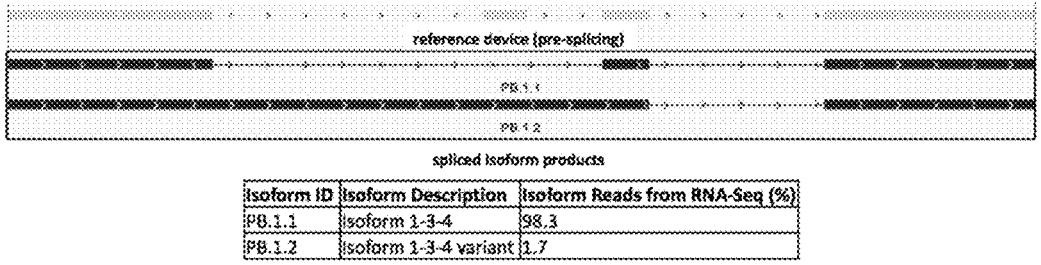
Figure 12:
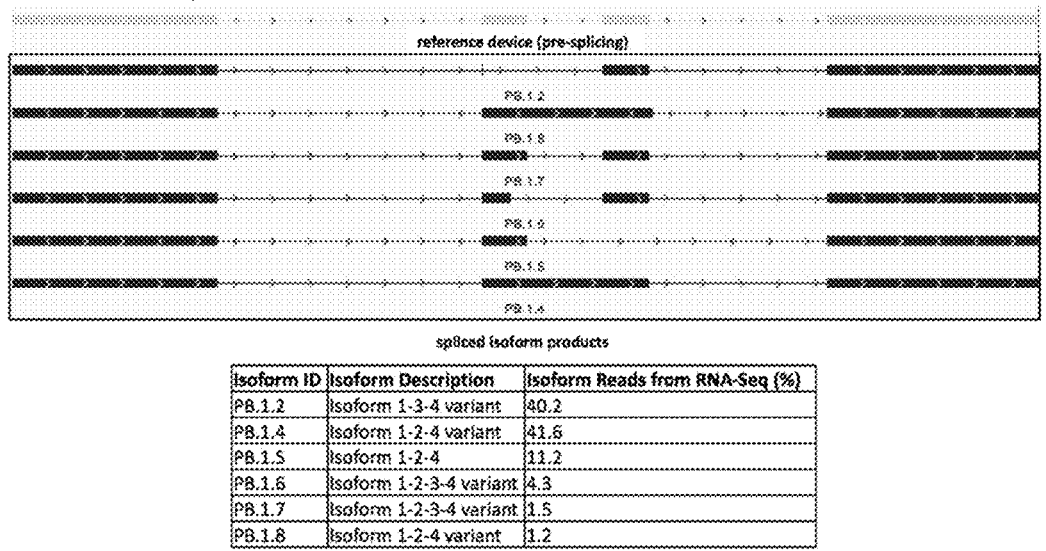
Figure 12:
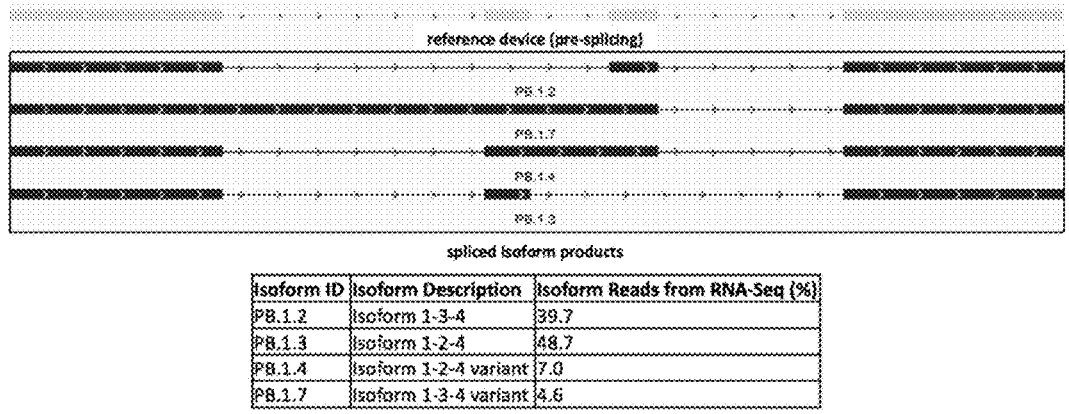
Figure 12:
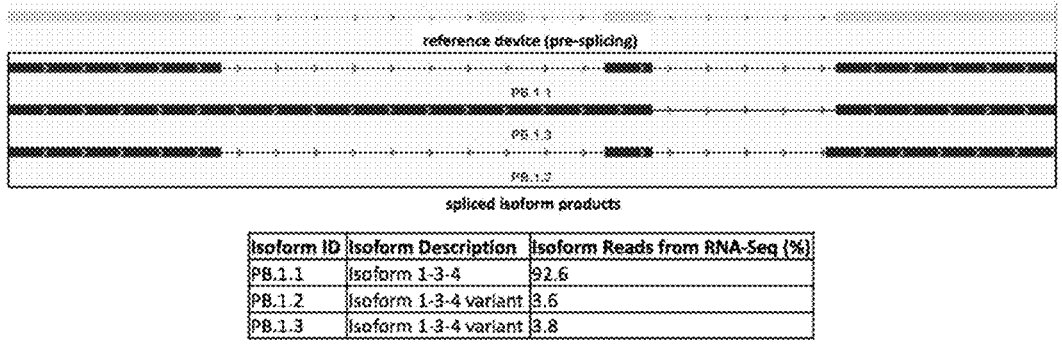

The Splicing Signature of Alternative Splicing Devices Derived from ASD GFP and ASD mCherry FIG. 12 shows the splicing signature of a number of alternative splicing devices derived from ASD GFP and ASD mCherry described in earlier examples. The signature was identified by RNA sequencing. The reference device (pre-splicing) is shown at the top in light gray and the isoform profile is illustrated in dark gray below. The distance between the arrows denotes 100 nt. Each isoform has an isoform ID, isoform description, and percentage of reads (as identified by RNA sequencing) from the splicing of the device associated with the isoform. The isoform description notes if the isoform splices correctly to one of four isoforms: (i) isoform 1-2-4, (ii) isoform 1-3-4, (iii) isoform 1-4, and (iv) isoform 1-2-3-4. If the isoform is a variant of one of these four isoforms, the variant is noted and determined by which of the middle exons is properly identified (i.e. if the 3' end of exon 2 is properly selected but the splicing downstream differs from the defined pattern, the isoform is an isoform 1-2-4 variant). The percentage of reads associated with any given isoform can range+/−20% (i.e. if a certain isoform is 30% of the spliced product, then that isoform could be present within the range of 10-50%).

Example 13

Figure 13:
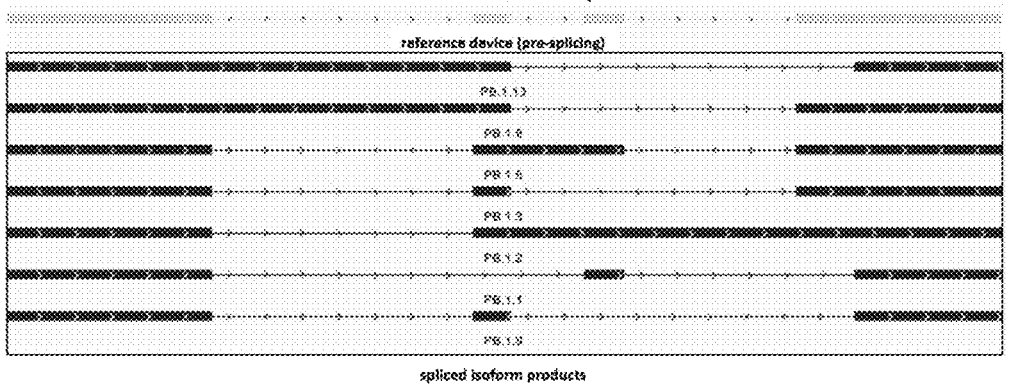
FIG. 13 shows the splicing signature of an alternative splicing device derived from ASD GFP with an integrated hairpin representative of an aptamer.

The Splicing Signature of an Alternative Splicing Device Derived from ASD GFP with an Integrated Hairpin Representative of an Aptamer FIG. 13 shows the splicing signature of two alternative splicing devices derived from ASD GFP that contain RNA hairpins in intron 1. The signature was identified by RNA sequencing. The reference device (pre-splicing) is shown at the top in light gray and the isoform profile is illustrated in dark gray below. The distance between the arrows denotes 100 nt. Each isoform has an isoform ID, isoform description, and percentage of reads (as identified by RNA sequencing) from the splicing of the device associated with the isoform. The isoform description notes if the isoform splices correctly to one of four isoforms: (i) isoform 1-2-4, (ii) isoform 1-3-4, (iii) isoform 1-4, and (iv) isoform 1-2-3-4. If the isoform is a variant of one of these four isoforms, the variant is noted and determined by which of the middle exons is properly identified (i.e. if the 3' end of exon 2 is properly selected but the splicing downstream differs from the defined pattern, the isoform is an isoform 1-2-4 variant). The percentage of reads associated with any given isoform can range+/−20% (i.e. if a certain isoform is 30% of the spliced product, then that isoform could be present within the range of 10-50%).

RNA hairpin 1 has the sequence "GGCGATAC-CACGGGAAACCGCCTTGGCTGCGCCAGAGA" (SEQ ID NO:5) and was incorporated in the ASD GFP exon 2 mutated BP+truncated PPT-13, exon 3 (FIG. 2C) mutated BP downstream of the truncated polypyrimidine tract and upstream of a 10 nt linker with sequence "TCTCATTTGC" (SEQ ID NO:6) followed by exon's 3' splice site. This unit is upstream of exon 2 and the isoform profile illustrates that an RNA hairpin with secondary structure similar to that of an aptamer, can be integrated near splicing elements within an intron. RNA hairpins can readily be replaced with ligand responsive aptamers to link splicing outcome to the presence of ligand.

TABLES

The tables presented in the following pages provide the sequences of and further information on many of the sequence elements described above.

TABLE 1

Sequence elements for alternative splicing devices

| SEQ ID NO: | Sequence element | Sequence (RNA, 5' → 3') |
|---|---|---|
| — | 5' splice site ▽ | AG * GU |
| | | AU * GU |
| — | 3' splice site ▼ | AG * GU |
| | | AG * GG |
| | | AG * GU |
| | | AG * GC |
| — | Branch point sequence ▮ | CUAAC |
| | | CGAUC |
| | | CGUUC |
| | | CCAAC |
| 7 | Polypyrimidine tract ☐ | CUGGCACCCGUUUGUUGUGUGUCUCACACCCGGUCCAUGCCGGCCGCC |
| | | CGCGCCCGCUCUCCGCUGUCCC |
| 8 | | UUUCUCUUUCUCUCUCCCUCCCUGUCUUUCCCUCUCUCUCUCUUUCCC |
| 9 | | UUUCUCUUUCUCUCUCCCUCCCUGUCUUUCCCUCUCUC |
| 10 | | UUUCUCUUUCUCUCUCCCUCCCUGUCUUUCCCU |
| 11 | | UUUCUCUUUCUCUCUCCCUCCCUGUCUU |
| 12 | | UUUCUCUUUCUCUCUCCCUCCCU |
| 13 | | UUUCUCUUUCUCUCUCCCC |
| 14 | | UUUCUCUUUCUCU |
| — | | UUUCUCUU |
| — | | UUUCU |
| — | | UUU |
| — | Insulator sequence | CAGGUC |
| — | | CAGCUC |
| — | | AAGGUA |
| — | | CAGCUG |
| — | | GAUGUA |
| — | | UAGGGC |
| — | | UAGGCU |
| — | | CAGGUC |
| — | | CAGGUA |
| 15 | Exon sizing sequence | CUCGGCUCCUCCGGCUCCUCC |
| 16 | | GGCUCCUCCGGCUCCUCCGAU |
| 17 | | CUCGGCUCCUCCGGCUCCUCCGGCUCCUCCGGCUCCUCC |
| 18 | | GGCUCCUCCGGCUCCUCCGGCUCCUCCGGCUCCUCCGAU |

TABLE 2

Exon sequences for alternative splicing devices

| SEQ. ID NO: | Exon Name | Sequence (DNA, 5' → 3') |
|---|---|---|
| 19 | ASD GFP - Clover Exon 1 | ATGGTGAGCAAGGGCGAGGAGCTGTTCACCGGGGTGGTGCCCATCCTGGTCGAGCTGGACGGCGACGTA AACGGCCACAAGTTCAGCGTCCGCGGCGAGGGCGAGGGCGATGCCACCAACGGCAAGCTGACCCTGAAG TTCATCTGCACCACCGGCAAGCTGCCCGTGCCCTGGCCCACCCTCGTGACCACCTTCGGCTACGGCGTGG CCTGCTTCAGCCGCTACCCCGACCACATGAAGCAGCACGACTTCTTCAAGTCCGCCATGCCCGAAGGCTA CGTCCAGGAGCGCACCATCTCTTTCAAGGACGACGGTACCTACAAGACCCGCGCCGAGGTGAAGTTCGA GGGCGACACCCTGGTGAACCGCATCGAGCTGAAGGGCATCGACTTCAAGGAGGACGGCAACATCCTGGG GCACAAGCTGGAGTACAACTTCAACAGCCACAACGTCTATATCACGGCCGACAAGCAGAAGAACGGCAT CAAGGCTAACTTCAAGATCCGCCACAACAAGCTTGAGGACGGCAGCGTGCAGCTCGCCGACCACTACCAGCA GAACACCCCcAUcGaGAGGGccccurGcrGcrucCGACAACCACCAG |
| 20 | ASD GFP - mCherry Exon 2 | CTCGTGAGCAAGGGCGAGGAGGATAACATGGCCATCATCAAGGAGTTCATGCGCTTCAAAGTGCACATG GAGGGCTCCGTGAACGGCCACGAGTTCGAGATCGAGGGCAAG |
| 21 | ASD GFP - Clover Exon 3 | CTGAGCCATCAGTTCCGCCCTGAGCAAAGACCCCAACGAGAAGCGCGATCACATGGTCCTGCTGGAGTTC GTGACCGCCGCCGGGATTACACATGGCATGGACGAGCTGTACAAGGAT |
| 22 | ASD GFP - mCherry Exon 4 | GGCGAGGGCCGCCCCTACGAGGGCACCCAGACCGCCAAGCTGAAAGTGACCAAGGGTGGCCCCCTGCCC TTCGCCTGGGACATCCTGTCCCCTCAGTTCATGTACGGCTCCAAGGCCTACGTGAAGCACCCCGCCGACA TCCCCGACTACTTGAAGCTGTCCTTCCCCGAGGGCTTCAAGTGGGAGCGCGTGATGAACTTCGAGGACG GCGGCGTGGTGACCGTGACCCAGGACTCCTCCCTGCAAGACGGCGAGTTCATCTACAAAGTGAAGCTGC GCGGCACCAACTTCCCCTCCGACGGCCCCGTAATGCAGAAGAAGACCATGGGCTGGGAGGCCTCCTCCG AGCGGATGTACCCCGAGGACGGCGCCCTGAAGGGCGAGATCAAGCAGAGGCTGAAGCTGAAGGACGGCG |

TABLE 2-continued

Exon sequences for alternative splicing devices

| SEQ. ID NO: | Exon Name | Sequence (DNA, 5' → 3') |
|---|---|---|
| | | GCCACTACGACGCTGAAGTCAAGACCACCTACAAGGCCAAGAAGCCCGTGCAGCTGCCCGGAGCCTACA ACGTCAACATCAAGTTGGACATCACCTCCCACAACGAGGACTACACCATCGTGGAACAGTACGAACGCG CCGAGGGCCGCCACTCCACCGGCGGCATGGACGAGCTGTACAAGTAA |
| 23 | ASD mCherry - mCherry Exon 1 | ATGGTGAGCAAGGGCGAGGAGGATAACATGGCCATCATCAAGGAGTTCATGCGCTTCAAAGTGCACAT GGAGGGCTCCGTGAACGGCCACGAGTTCGAGATCGAGGGCGAGGGCGAGGGCCGCCCCTACGAGGGCAC CCAGACCGCCAAGCTGAAAGTGACCAAGGGTGGCCCCTGCCCTTCGCCTGGGACATCCTGTCCCCTCAG TTCATGTACGGCTCCAAGGCCTACGTGAAGCACCCCGCCGACATCCCCGACTACTTGAAGCTGTCCTTCC CCGAGGGCTTCAAGTGGGAGCGCGTGATGAACTTCGAGGACGGCGGCGTGGTGACCGTGACCCAGGACT CCTCCCTGCAGGACGGCGAGTTCATCTACAAAGTGAAGCTGCGCGGCACCAACTTCCCTCCGACGGCCC CGTAATGCAGAAGAAGACCATGGGCTGGGAGGCCTCCTCCGAGCGGATGTACCCCGAGGACGGCGCCCT GAAGGGCGAGATCAAGCAGAGGCTGAAGCTGAAGGACGGCGGCCACTACGACGCTGAAGTCAAGACCA CCTACAAGGCCAAGAAGCCCGTGCAG |
| 24 | ASD mCherry - Clover Exon 2 | CTCGTGAGCAAGGGCGAGGAGCTGTTCACCGGGGTGGTGCCCATCCTGGTCGAGCTGGACGGCGACGTA AACGGCCACAAGTTCAGCGTCCGCGGGCGAGGGCGAGGGCGATGCCACCAACGGCAAG |
| 25 | ASD mCherry - mCherry Exon 3 | CTGCCCGGAGCCTACAACGTCAACATCAAGTTGGACATCACCTCCCACAACGAGGACTACACCATCGTG GAACAGTACGAACGCGCCGAGGGCCGCcAcraAccGGCGGCATGGACGAGCTGTACAAGGAT |
| 26 | ASD mCherry - Clover Exon 4 | GCTACCCTGAAGTTCATCTGCACCACCGGCAAGCTGCCCGTGCCCTGGCCCACCCTCGTGACCACCTTCG GCTACGGCGTGGCCTGCTTCAGCCGCTACCCCGACCACATGAAGCAGCACGACTTCTTCAAGTCCGCCAT GCCCGAAGGCTACGTCCAGGAGCGCACCATCTCTTTCAAGGACGACGGTACCTACAAGACCCGCGCCGA GGTGAAGTTCGAGGGCGACACCCTGGTGAACCGCATCGAGCTGAAGGGCATCGACTTCAAGGAGGACGG CAACATCCTGGGGCACAAGCTGGAGTACAACTTCAACAGCCACAACGTCTATATCACGGCCGACAAGCA GAAGAACGGCATCAAGGCTAACTTCAAGATCCGCCACAACGTTGAGGACGGCAGCGTGCAGCTCGCCGA CCACTACCAGCAGAACACCCCcAnGGCGACGGCCCCGTGCTGCTGCCCGACAACCAcTACCTGAGCCAT CAGTCCGCCCTGAGCAAAGACCCCAACGAGAAGCGCGATCACATGGTCCTGCTGGAGTTCGTGACCGCC GCCGGGATTACACATGGCATGGACGAGCTGTACAAGTAA |
| 27 | ASD TALE 1 - Exon 1 | ATGTCGCGGACCCCGGCTCCCTTCCCCACCCGCACCCAGCCCAGCGTTTTCGGCCGACTCGTTCTCAGACC TGCTTAGGCAGTTCGACCCCTCACTGTTTAACACATCGTTGTTCGACTCCCTTCCTCCGTTTGGGGCGA CCATACGGAGGCGGCCACCGGGGAGTGGGATGAGGTGCAGTCGGATTGAGAGCTGCGGATGCACCACC CCCAACCATGCGGGTGGCCGTCACCGCTGCCCGACCGCGAGGGCGAAGCCCGCACCAAGGCGGAGGGC AGCGCAACCGTCCGACGCAAGCCCCGCAGCGCAAGTAGATTTGAGAACTTTGGGATATTCACAGCAGCA GCAGGAAAAGATCAAGCCCAAAGTGAGGTCGACAGTCGCGCAGCATCACGAAGCGCTGGTGGGTCATGG GTTTACACATGCCCACATCGTAGCCTTGTCGCAGCACCTGCAGCCCTTGGCACGGTCGCCGTCAAGTAC CAGGACATGATTGCGGCGTTGCCGGAAGCCACACATGAGGCGATCGTCGGTGTGGGGAAACAGTGGAGC GGAGCCCGAGCGCTTGAGGCCCTGTTGACGGTCGCGGGAGAGCTGAGAGGGCCTCCCCTTCAGCTGGAC ACGGGCCAGTTGCTGAAGATCGCGAAGCGGGGAGGAGTCACGGCGGTCGAGGCGGTGCACGCGTGGCGC AATGCGCTCACGGGAGCACCCCTCAACCTGACCCCAGAGCAGGTCGTGGCAATCGCCTCCAACATTGGC GGGAAACAGGCACTCGAGACTGTCCAGCGCCTGCTTCCCGTGCTGTGCCAAGCGCACGGACTCACCCCA GAGCAGGTCGTGGCGATCGCAAGCCACGACGGAGGAAAGCAAGCCTTGGAAACAGTACAGAGGCTGTT GCCTGTGCTGTGCCAAGCGCACGGCCTCACCCCAGAGCAG |
| 28 | ASD TALE 1 - Exon 2 | GTCGTGGCAATCGCGAGCAATAACGGCGGAAAACAGGCTTTGGAAACGGTGCAGAGGCTCCTTCCAGTG CTGTGCCAAGCGCACGGATTAACCCCAGAGCAGGTCGTGGCAATCGCCTCCAACATTGGCGGGAAACAG |
| 29 | ASD TALE 1 - Exon 3 | GTCGTGGCAATCGCGAGCAATGGAGGCGGAAAACAGGCTTTGGAAACGGTGCAGAGGCTCCTTCCAGTG CTGTGCCAAGCGCACGGATTAACCCCAGAGCAGGTCGTGGCAATCGCCTCCAACATTGGCGGGAAACAG |
| 26 | ASD TALE 1 - Exon 4 | GCTACCCTGAAGTTCATCTGCACCACCGGCAAGCTGCCCGTGCCCTGGCCCACCCTCGTGACCACCTTCG GCTACGGCGTGGCCTGCTTCAGCCGCTACCCCGACCACTGAAGCAGCACGACTTCTTCAAGTCCGCCAT GCCCGAAGGCTACGTCCAGGAGCGCACCATCTCTTTCAAGGACGACGGTACCTACAAGACCCGCGCCGA GGTGAAGTTCGAGGGCGACACCCTGGTGAACCGCATCGAGCTGAAGGGCATCGACTTCAAGGAGGACGG CAACATCCTGGGGCACAAGCTGGAGTACAACTTCAACAGCCACAAGCTCTATATCACGGCCGACAAGCA GAAGAACGGCATCAAGGCTAACTTCAAGATCCGCCACAACGTTGAGGACGGCAGCGTGCAGCTCGCCGA CCACTACCAGCAGAACACCCCCATCGGCGACGGCCCCGTGCTGCTGCCCGACAACCACTACCTGAGCCAT CAGTCCGCCCTGAGCAAAGACCCCAACGAGAAGCGCGATCACATGGTCCTGCTGGAGTTCGTGACCGCC GCCGGGATTACACATGGCATGGACGAGCTGTACAAGTAA |
| 30 | ASD PKM - Exon 1 | ATGCTGGAGAGCATGATCAAGAAGCCCGCCCCACTCGGGCTGAAGGCAGTGATGTGGCCAATGCAGTC CTGGATGGAGCCGACTGCATCATGCTGTCTGGAGAAACAGCCAAAGGGGACTATCCTCTGGAGGCTGTG CGCATGCAGCACCTG |
| 31 | ASD PKM - Exon 2 | ATAGCtCGTGAGGCTGAGGCAGCCATUTCCACCGCAAGCTGTFTGAAGAACTTGTGCGAGCCTCAAGT CACTCCACAGACCTCATGGAAGCCATGGCCATGGGCAGCGTGGAGGCTTCTTATAAGTGTTTAGCAGCA GCTTTGATAGTTCTGACGGAGTCTGGCAG |
| 32 | ASD PKM - Exon 3 | ATTGCCCGTGAGGCAGAGGCTGCCATCTACCACTTGCAATTATTTGAGGAACTCCGCCGCCTGGCGCCC ATTACCAGCGACCCCACAGAAGCCACCGCCGTGGGTGCCGTGGAGGCCTCCTTCAAGTGCTGCAGTGGG GCCATAATCGTCCTCACCAAGTCTGGCAG |

TABLE 2-continued

Exon sequences for alternative splicing devices

| SEQ. ID NO: | Exon Name | Sequence (DNA, 5' → 3') |
|---|---|---|
| 33 | ASD PKM - Exon 4 | GTCTGCTCACCAGGCGGCCAGATACCGCCCACGTGCCCCCATCATTGCTGTGACCCGGAATCCCCAGACA GCTCGTCAGGCCCACCTGTACCGTGGCATCTTCCCTGTGCTGTGCAAGGACCCAGTCCAGGAGGCCTGGG CTGAGGACGTGGACCTCCGGGTGAACTTTGCCATGAATGTTTAA |
| 34 | ASD FGFR2 - Exon 1 | ATGGCTGGACTGCCTGCAAATGCCTCCACGGTGGTCGGAGGGGACGTAGAATTTGTCTGCAAGGTTTAT AGTGATGCCCAGCCCCATATCCAGTGGATCAAACATGTGGAAAAGAACGGCAGTAAATATGGACCTGA TGGGCTGCCCTACCTCAAGGTCCTGAAG |
| 35 | ASD FGER2 - Exon 2 | CACTCGGGGATAAATAGCTCCAATGCAGAAGTGCTGGCTCTGTTCAATGTGACGGAGATGGATGCTGGG GAATATATATGTAAGGTCTCCAATTATATAGGGCAGGCCAACCAGTCTGCCTGGCTCACTGTCCTGCCC AAACAGCAAG |
| 36 | ASD FGER2 - Exon 3 | GCCGCCGGTGTTAACACCACGGACAAAGAAATTGAGGTTCTCTATATTCGGAATGTAACTTTTGAGGAT GCTGGGGAATATACGTGCTTGGCGGGTAATTCTATCGGGATATCCTTTCACTCTGCATGGTTGACAGTT CTGCCAG |
| 37 | ASD FGER2 - Exon 4 | CACCTGTGAGAGAGAAGGAGATCACAGCTTCCCCAGATTACCTGGAGATAGCTATTTACTGCATAGGGG TCTTCTTAATCGCCTGCATGGTGGTGACAGTCATCTTTTGCCGAATGAAGACCACGACCAAGAAGCCAG ACTTCAGCAGCCAGCCAGCTGTGCACAAGCTGACCAAGCGCTAA |

TABLE 3

Intron sequences for alternative splicing devices

| SeqID | Intron Name | Sequence (DNA, 5' → 3') |
|---|---|---|
| 38 | ASD Intron 1 | GTCTGCGTCTACCCCCAACCCCCACTGCCCCAACTCCGCGTCAGTCTCTCAGTCCGGGAACCCGAACTGG CTCCCTTTCCCCATCCTATCCCCAGCACAGGATGTCCAGGGGCGCGCATTTAAAAAAAAAATTAGGAGA AGAAGCTCGAGAGTTAGACTGATTCTAACTTTTCTGTCTCGCCTGAGGACGCTTGTGGCCCTTCTCTGG CTCCCACGGTCCGCGAAGTCCACTGGAATTCCCCGTAAAGAGGCTCTTGACTCTTAGGATTGGGGATCA GTTTTGAAAGAGGAAGGGAGAAAGGATACAAGTTCCCGGGATGCCTGGAGGGAAGGGCGGGGGAGCGG GGCAAGGATTAAGTCCTAAGGTGTCCGAAGTTCTTTGGACCTTTTGGTTGGGGAGAGAGCCCTTAAG ATGGGATTGAAAACTTTGAAGCGCACTGAATTATTTCCTAAGAACAAAGATGGGACAGAATGGGAGAC ACAGACGGAAAGCTAGCCAAACAAGGGCGTGTTTCTTCAATCCCTCAAGTTGGGGACCTGAGCTTGCTG TCTTCGGCCGAGCGTGTGGTCCCGGGGTGGCGTGGGGTGGGGGGTGGGATGCGAGATGAGTCACTGAGT GGTTCCAGCTCTGGGAGAGAGATTACCTAGGGTCCCTTGAGCCCCAAAGCAGCGATCCCTTAGCCCCAG GACCCCAGCCAACCTGGCACCCGTTTGTTGTGTGTCTCACACCCGGTCCATGCCGGCCGCCCGCGCCCGC TCTCCGCTGTCCCAG |
| 39 | ASD Intron 2 | GTACCCGGGCGCGGTGTGGCACTGCACACGAATGGCTAACTTTCTCTTTCTCTCTCCCTCCCTGTCTT TCCCTCTCTCTCTTTCCCGCTGTCCCTGTCCTTTATGGTCTACGCACCCTCAACCCGCACCTTGCGGG ATCACGCTGCCTGCTGCACCCCACCCCCTTCCCCCTTCCTTCCCCCACCCCCGTACTC-CACTGCCAACTC CCAG |
| 40 | ASD Intron 3 | GTAAGTGCACGCTCACACTGCCTCCCTCACCCCCTGACCGCGTGGCCGCTCTGGGGGTCACCACAGGGGC TGCAGAGCAAAGGAAGAGGGTGATCCTCCTCCTACAGGACACCTGCACACAGCCTGGCCATAGCCCAGA GCACTGGATGCCGCCTCTGCTGCTGCGCACATTTCATTTATATTCTGTCCTTTCCCCTTTTTCTCCTCTT CTTTACCTCCTCCCCTTTGGTTGGAGGTGGGTGGGTGAGAAGCTGGGGAACACGGCCTCTGAAATGGGG ACTGCTGGAAGTGAACTTCGCCTCCTGCTGGTATAAAACCGCTGAAGTGTATGTCATCACCAAGGTCTG TACAAAACAGAATCCCTAGTGTTCTTGTTTGCCACCCTACCCCCAAAACCCCGGTGGTTTTCGCTGAT GGACCTAGTCTGAGTGGGTTCAGAGAGCCTGACCTTTGGAATTCCTCACTTTCTCCCCATCTCTGAGTG TCTTTCATCCTCTGCCTAG |

TABLE 4

List of alternative splicing devices
A list of plasmids used in the examples are summarized below, note that not all the plasmids are included in the table below.

| SeqID | Device Name |
|---|---|
| pCS3434 | ASD GFP |
| pCS3435 | ASD GFP exon 2 mutated BP + PPT |
| pCS3436 | ASD GFP exon 2 mutated BP + PPT, exon 3 mutated BP |
| pCS3437 | ASD GFP exon 2 mutated BP + truncated PPT-13, exon 3 mutated BP |
| pCS3438 | ASD GFP exon 2 mutated BP + truncated PPT-8, exon 3 mutated BP |

TABLE 4-continued

List of alternative splicing devices
A list of plasmids used in the examples are summarized below, note that not all the plasmids are included in the table below.

| SeqID | Device Name |
|---|---|
| pCS3439 | ASD GFP exon 3 deletion |
| pCS3440 | ASD GFP Int1-300-Int3-200 |
| pCS3441 | ASD mCherry |
| pCS3442 | ASD mCherry exon 2 mutated BP + PPT |
| pCS3443 | ASD mCherry exon 2 mutated BP + truncated PPT-5, exon 3 mutated BP |

TABLE 4-continued

List of alternative splicing devices
A list of plasmids used in the examples are summarized below,
note that not all the plasmids are included in the table below.

| SeqID | Device Name |
|---|---|
| pCS3444 | ASD mCherry exon 2 mutated BP + truncated PPT-3, exon 3 mutated BP |
| pCS3445 | ASD mCherry exon3 deletion |
| pCS3446 | ASD mCherry exon 3 PPT-8 |
| pCS3447 | ASD GFP exon 2 mutated BP + truncated PPT-13 + RNA hairpin 1, exon 3 mutated BP |
| pCS3448 | ASD GFP exon 2 mutated BP + truncated PPT-13 + RNA hairpin 2, exon 3 mutated BP |

TABLE 5

Small molecule and protein aptamer sequences

| Aptamer Name | Sequence (DNA, 5' → 3') | Reference |
|---|---|---|
| Folinic Acid (FA8-4) | GGGACTTCTGCCCGCCTCCTTCCTGCTCGTGTCAAAATGAATGGCGCTCGGC GTTGCGTGGTACGTTATATTCCGGCCAAGCAGCCATTCATGGGAGACGAGAT AGGCGGACAC (SEQ ID NO: 41) | Chang Al., Ph.D. Thesis, Chapter 4, Stanford University 2014 |
| Folinic Acid (FA8-3) | GGGACTTCTGCCCGCCTCCTTCCGCTGAGGACTCGGCACCGAATTTGCCAACG TCTGGTCACGACCGTAGTACACTACCCCTCGAAATCACGAGGGAGACGAGAT AGGCGGACAC (SEQ ID NO: 42) | Chang Al., Ph.D. Thesis, Chapter 4, Stanford University 2014 |
| Folinic Acid (FA8-11) | GGGACTTCTGCCCGCCTCCTTCCGCTTACCGGACGCCTTAAGGCATCAGCATG CAGTGCTTGGTACGTTATATTCAGCTGCAACTCGGGATGCGGAGACGAGATA GGCGGACAC (SEQ NO: 43) | Chang Al., Ph.D. Thesis, Chapter 4, Stanford University 2014 |
| Theophylline | GGTGATACCAGCCGAAAGGCCCTTGGCAGCACC (SEQ ID NO: 44) | Lynch et al, Chem & Biol 14, 173, 2007 |
| MS2 | CGTACACCATCAGGGTACG (SEQ ID NO: 45) | Villemaire et al, J Biol Chem 278, 50031, 2003 |
| β-catenin | AGGCCGATCTATGGACGCTATAGGCACACCGGATACTITAACGATTGGCT (SEQ ID NO: 46) | Lee et al, Cancer Res 66, 10560, 2006 |

TABLE 6

Small molecule responsive ribozymes

| Ribozyme | Sequence (DNA, 5' → 3') | Reference |
|---|---|---|
| L2b8 (Theophylline responsive ON switch) | GCTGTCACCGGATGTGCTTTCCGGTCTGATGAGTCCGTTGTCCATACCAGCA TCGTCTTGATGCCCTTGGCAGGGACGGGACGGAGGACGAAACAGC (SEQ ID NO: 47) | Chen et al, PNAS 107, 8531, 2010 |
| L2bulge18tc (Tetracycline responsive ON switch) | GCTGTCACCGGATGTGCTTTCCGGTCTGATGAGTCCGTTGTCCAAAACATAC CAGATTTCGATCTGGAGAGGTGAAGAATTCGACCACCTGGACGAGGACGAG GACGAAACAGC (SEQ ID NO: 48) | Chen et al, PNAS 107, 8531, 2010 |

TABLE 7

Annotated ASD GIP (SEQ ID NO: 49)
Sequence elements (bold) within the alternative splicing device are from
Table 1, exon sequences (underlined) are from Table 2, and intron sequences
are from Table 3. Aptamers, like examples shown in Table 4, can be
incorporated at any position within the intron, and may be separated from
a sequence element or regulatory element by a linker sequence. Ribozymes,
like examples shown in Table 5, can be incorporated atposition within an
intron, or in an untranslated region upstream or downstream of the
alternative splicing device.

(SEQ. ID NO: 49)
CGCCACCATGGTGAGCAAGGGCGAGGAGCTGTTCACCGGGGTGGTGCCCATCCTGGTCGAGCTGGACGGCGACGT

AAACGGCCACAAGTTCAGCGTCCGCGGCGAGGGCGAGGGCGATGCCACCAACGGCAAGCTGACCCTGAAGTTCAT

CTGCACCACCGGCAAGCTGCCCGTGCCCTGGCCCACCCTCGTGACCACCTTCGGCTACGGCGTGGCCTGCTTCAGC

TABLE 7-continued

Annotated ASD GIP (SEQ ID NO: 49)
Sequence elements (bold) within the alternative splicing device are from Table 1, exon sequences (underlined) are from Table 2, and intron sequences are from Table 3. Aptamers, like examples shown in Table 4, can be incorporated at any position within the intron, and may be separated from a sequence element or regulatory element by a linker sequence. Ribozymes, like examples shown in Table 5, can be incorporated atposition within an intron, or in an untranslated region upstream or downstream of the alternative splicing device.

<u>CGCTACCCCGACCACATGAAGCAGCACGACTTCTTCAAGTCCGCCATGCCCGAAGGCTACGTCCAGGAGCGACCA</u>

<u>TCTCTTTCAAGGACGACGGTACCTACAAGACCCGCGCCGAGGTGAAGTTCGAGGGCGACACCCTGGTGAACCGCA</u>

<u>TCGAGCTGAAGGGCATCGACTTCAAGGAGGACGGCAACATCCTGGGGCACAAGCTGGAGTACAACTTCAACAGCC</u>

<u>ACAACGTCTATATCACGGCCGACAAGCAGAAGAACGGCATCAAGGCTAACTTCAAGATCCGCCACAACGTTGAGG</u>

<u>ACGGCAGCGTGCAGCTCGCCGACCACTACCAGCAGAACACCCCCATCGGCGACGGCCCCGTGCTGCTGCCCGACA</u>

<u>ACCAC</u>CAGGTCTGCGTCTACCCCCAACCCCCACTGCCCCAACTCCGCGTCAGTCTCTCAGTCCGGGAACCCGAACT

GGCTCCCTTTCCCCATCCTATCCCCAGCACAGGATGTCCAGGGGCGCGCATTTAAAAAAAAAATTAGGAGAAGAA

GCTCGAGAGTTAGACTGATTCTAACTTTTCTGTCTCGCCTGAGGACGCTTGTGGCCCTTCTCTGGCTCCCACGGTCC

GCGAAGTCCACTGGAATTCCCCGTAAAGAGGCTCTTGACTCTTAGGATTGGGGATCAGTTTTGAAAGAGGAAGGG

AGAAAGGATACAAGTTCCCGGGATGCCTGGAGGGAAGGGCGGGGAGCGGGGCAAGGATTAAGTCCTAAGGTGT

CCGAAGTTCTTTGGACCTTTTGGTTGGGGAGAGAGAGCCCTTAAGATGGGATTGAAAACTTTGAAGCGCACTGAAT

TATTTCCTAAGAACAAAGATGGGACAGAATGGGAGACACAGACGGAAAGCTAGCCAAACAAGGGCGTGTTTCTTC

AATCCCTCAAGTTGGGGACCTGAGCTTGCTGTCTTCGGCCGAGCGTGTGGTCCCGGGGTGGCGTGGGGTGGGGGT

GGGATGCGAGATGAGTCACTGAGTGGTTCCAGCTCTGGGAGAGATTACCTAGGGTCCCTTGAGCCCCAAAGCA

GCGATCCCTTAGCCCCAGGACCCCAGCCAACCTGGCACCCGTTTGTTGTGTGTCTCACACCCGGTCCATGCCG

GCCGCCCGCGCCCGCTCTCCGCTGTCCCAGCT<u>CGTGAGCAAGGGCGAGGAGGATAACATGGCCATCATCAAGG</u>

<u>AGTTCATGCGCTTCAAAGTGCACATGGAGGGCTCCGTGAACGGCCACGAGTTCGAGATCGAGGGC</u>AAGGTACCCG

GGCGCGCGGTGTGGCACTGCACACGAATGGCTAACTTTCTCTTTCTCTCTCCCTCCCTGTCTTTCCCTCTCTCT

CTCTTTCCCGCTGTCCCTGTCCTTTATGGTCTACGCACCCTCAACCCGCACCTTGCGGGATCACGCTGCCTGCTGCA

CCCCACCCCCTTCCCCCTTCCTTCCCCCCACCCCCGTACTCCACTGCCAACTCCCAGCTG<u>AGCCATCAGTCCGCCCT</u>

<u>GAGCAAAGACCCCAACGAGAAGCGCGATCACATGGTCCTGCTGGAGTTCGTGACCGCCGCCGGGATTACACATGG</u>

<u>CATGGACGAGCTGTACAAG</u>GATGTAAGTGCACGCTCACACTGCCTCCCTCACCCCCTGACCGCGTGGCCGCTCTGG

GGGTCACCACAGGGGCTGCAGAGCAAAGGAAGAGGGTGATCCTCCTCCTACAGGACACCTGCACACAGCCTGGCC

ATAGCCCAGAGCACTGGATGCCGCCTCTGCTGCTGCGCACATTTCATTTATATTCTGTCCTTTCCCCTTTTTCTCCTC

TTCTTTACCTCCTCCCCTTTGGTTGGAGGTGGGTGGGTGAGAAGCTGGGGAACACGGCCTCTGAAATGGGGACTGC

TGGAAGTGAACTTCGCCTCCTGCTGGTATAAAACCGCTGAAGTGTATGTCATCACCAAGGTCTGTACAAAACAGAA

TCCCTAGTGTTCTTGTTTGCCACCCTACCCCCAAAACCCCCGGTGGTTTTCGCTGATGGACCTAGTCTGAGTGGGTT

CAGAGAGCCTGACCTTTGGAATTCCTCACTTTCTCCCCATCTCTGAGTGTCTTTCATCCTCTGCCTAGGGC<u>GAGGGC</u>

<u>CGCCCCTACGAGGGCACCCAGACCGCCAAGCTGAAAGTGACCAAGGGTGGCCCCCTGCCCTTCGCCTGGGACATC</u>

<u>CTGTCCCCTCAGTTCATGTACGGCTCCAAGGCCTACGTGAAGCACCCCGCCGACATCCCCGACTACTTGAAGCTGT</u>

<u>CCTTCCCCGAGGGCTTCAAGTGGGAGCGCGTGATGAACTTCGAGGACGGCGGCGTGGTGACCGTGACCCAGGACT</u>

<u>CCTCCCTGCAAGACGGCGAGTTCATCTACAAAGTGAAGCTGCGCGGCACCAACTTCCCCTCCGACGGCCCCGTAAT</u>

<u>GCAGAAGAAGACCATGGGCTGGGAGGCCTCCTCCGAGCGGATGTACCCCGAGGACGGCGCCCTGAAGGGCGAGAT</u>

<u>CAAGCAGAGGCTGAAGCTGAAGGACGGCGGCCACTACGACGCTGAAGTCAAGACAACCTACAAGGCCAAGAAGC</u>

<u>CCGTGCAGCTGCCCGGAGCCTACAAGCTCAACATCAAGTTGGACATCACCTCCCACAACGAGGACTACACCATCGT</u>

TABLE 7-continued

Annotated ASD GIP (SEQ ID NO: 49)
Sequence elements (bold) within the alternative splicing device are from Table 1, exon sequences (underlined) are from Table 2, and intron sequences are from Table 3. Aptamers, like examples shown in Table 4, can be incorporated at any position within the intron, and may be separated from a sequence element or regulatory element by a linker sequence. Ribozymes, like examples shown in Table 5, can be incorporated atposition within an intron, or in an untranslated region upstream or downstream of the alternative splicing device.

GGAACAGTACGAACGCGCCGAGGGCCGCCACTCCACCGGCGGCATGGACGAGCTGTACAAGTAACTGATCATAAG

CGGCCGC

What is claimed is:

1. A method of altering splicing in a cell, comprising:
   in a eukaryotic cell, contacting an RNA that comprises:
   i. in order: a first exon, a first intron, a second exon, a second intron, a third exon, a third intron, and a fourth exon, and
   ii. an aptamer that is present in the first and/or second introns,
   with a ligand for the aptamer to alter a ratio of a first splicing product and a second splicing product, wherein:
   the first splicing product comprises the first exon, the second exon and the fourth exon, but not the third exon, and
   the second splicing product comprises the first exon, the third exon, and the fourth exon, but not the second exon.

2. The method of claim 1, wherein the ligand is added exogenously to the cell.

3. The method of claim 1, wherein the ligand is generated endogenously within the cell.

4. The method of claim 1, wherein the first splicing product and the second splicing product encode different fluorescent proteins and the method comprises detecting expression of the different fluorescent proteins by the cell.

5. The method of claim 4, wherein the cell is present in a multicellular organism and the detecting is done in vivo.

6. The method of claim 1, wherein the first splicing product and the second splicing product encode different transcription factors, thereby changing transcription within the cell.

7. The method of claim 1, wherein said eukaryotic cell is a cell of a multicellular organism.

8. The method of claim 1, wherein said eukaryotic cell is a mammalian cell.

9. The method of claim 1, wherein the aptamer is within 200 bases of a sequence that regulates splicing of the first intron.

10. The method of claim 1, wherein, in the second intron, a 5' splice junction is less than 50 nucleotides from a branch point sequence.

11. The method of claim 1, wherein the RNA comprises one or more further exons in addition to the first, second, third and fourth exons.

12. The method of claim 11, wherein the one or more further exons are 5' of the first exon, between the third and fourth exons, and/or 3' of the fourth exon.

13. The method of claim 1, wherein the ligand for the aptamer is a small molecule.

14. The method of claim 1, wherein the ligand for the aptamer is a protein.

15. The method of claim 1, wherein the ligand for the aptamer is a nucleic acid.

16. The method of claim 1, wherein one or more intron/exon junctions of the RNA comprises an insulator.

17. The method of claim 1, wherein the RNA comprises a ligand-activatable ribozyme that degrades the RNA in the presence of a second ligand.

\* \* \* \* \*